(12) United States Patent
Marnfeldt

(10) Patent No.: US 12,383,744 B2
(45) Date of Patent: *Aug. 12, 2025

(54) CIRCUITRY TO ASSIST WITH NEURAL SENSING IN AN IMPLANTABLE STIMULATOR DEVICE

(71) Applicant: Boston Scientific Neuromodulation Corporation, Valencia, CA (US)

(72) Inventor: Goran N. Marnfeldt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/596,377

(22) Filed: Mar. 5, 2024

(65) Prior Publication Data

US 2024/0245918 A1    Jul. 25, 2024

Related U.S. Application Data

(63) Continuation of application No. 18/171,597, filed on Feb. 20, 2023, now Pat. No. 11,931,579, which is a
(Continued)

(51) Int. Cl.
*A61N 1/02* (2006.01)
*A61B 5/24* (2021.01)
(Continued)

(52) U.S. Cl.
CPC ............ *A61N 1/36125* (2013.01); *A61B 5/24* (2021.01); *A61N 1/025* (2013.01); *A61N 1/08* (2013.01);
(Continued)

(58) Field of Classification Search
CPC ...... A61N 1/36125; A61N 1/025; A61N 1/08; A61N 1/36135; A61N 1/371;
(Continued)

(56) References Cited

U.S. PATENT DOCUMENTS

| 4,811,738 A | 3/1989 | Economides et al. |
| 5,697,958 A | 12/1997 | Paul et al. |

(Continued)

FOREIGN PATENT DOCUMENTS

| EP | 3216489 | 9/2017 |
| WO | 95/07114 | 3/1995 |

(Continued)

OTHER PUBLICATIONS

H. Mino & J. Rubenstein, "Effects of Neural Refractoriness on Spatio-Temporal Variability in Spike Initiations with Eletrical Stimulation," IEEE Trans. On Neural Sys. & Rehabilitation Eng., vol. 14, No. 3, pp. 273-280 (2006).

(Continued)

*Primary Examiner* — Carl H Layno
*Assistant Examiner* — Anh-Khoa N Dinh
(74) *Attorney, Agent, or Firm* — Lewis & Reese, PLLC

(57) ABSTRACT

Passive tissue biasing circuitry in an Implantable Pulse Generator (IPG) is disclosed to facilitate the sensing of neural responses by holding the voltage of the tissue to a common mode voltage (Vcm). The IPG's conductive case electrode, or any other electrode, is passively biased to Vcm using a capacitor, as opposed to actively driving the (case) electrode to a prescribed voltage using a voltage source. Once Vcm is established, voltages accompanying the production of stimulation pulses will be referenced to Vcm, which eases neural response sensing. An amplifier can be used to set a virtual reference voltage and to limit the amount of current that flows to the case during the production of Vcm. In other examples, circuitry can be used to monitor the virtual reference voltage as useful to enabling the sensing the neural responses, and as useful to setting a compliance voltage for the current generation circuitry.

20 Claims, 18 Drawing Sheets

Related U.S. Application Data continuation of application No. 17/323,748, filed on May 18, 2021, now Pat. No. 11,607,549, which is a continuation of application No. 16/282,137, filed on Feb. 21, 2019, now Pat. No. 11,040,202.

(60) Provisional application No. 62/650,844, filed on Mar. 30, 2018.

(51) Int. Cl.
*A61N 1/08* (2006.01)
*A61N 1/36* (2006.01)
*A61N 1/37* (2006.01)
*A61N 1/378* (2006.01)

(52) U.S. Cl.
CPC ......... *A61N 1/36135* (2013.01); *A61N 1/371* (2013.01); *A61N 1/36153* (2013.01); *A61N 1/378* (2013.01)

(58) Field of Classification Search
CPC ............... A61N 1/36153; A61N 1/378; A61N 1/36139; A61N 1/0534; A61N 1/36034; A61N 1/36062; A61N 1/0452; A61N 1/0456; A61N 1/0551; A61N 1/36003; A61N 1/3603; A61N 1/0531; A61N 1/0539; A61N 1/3605; A61N 1/36142; A61N 1/36157; A61N 1/372; A61N 1/3756; A61N 1/3782; A61B 5/24; A61B 5/294; A61B 5/4836; A61B 2562/046; A61B 5/287; A61B 5/293; A61B 5/30; A61B 5/305; A61B 5/311; A61B 5/4848; A61B 5/686; A61B 5/7203; A61B 5/7225; A61B 5/7264

See application file for complete search history.

(56) References Cited

U.S. PATENT DOCUMENTS

| | | | |
|---|---|---|---|
| 5,702,429 A | 12/1997 | King | |
| 5,757,167 A * | 5/1998 | Arora | G05F 1/59 323/224 |
| 5,902,236 A | 5/1999 | Iversen | |
| 5,902,249 A | 5/1999 | Lyster | |
| 5,913,882 A | 6/1999 | King | |
| 6,181,969 B1 | 1/2001 | Gord | |
| 6,516,227 B1 | 2/2003 | Meadows et al. | |
| 6,560,490 B2 | 5/2003 | Grill et al. | |
| 7,024,247 B2 | 4/2006 | Gliner et al. | |
| 7,424,322 B2 | 9/2008 | Lombardi et al. | |
| 7,444,181 B2 | 10/2008 | Shi et al. | |
| 7,450,992 B1 | 11/2008 | Cameron | |
| 8,255,057 B2 | 8/2012 | Fang et al. | |
| 8,335,664 B2 | 12/2012 | Eberle | |
| 8,352,030 B2 | 1/2013 | Denison | |
| 8,606,362 B2 | 12/2013 | He et al. | |
| 8,620,436 B2 | 12/2013 | Parramon et al. | |
| 9,044,155 B2 | 6/2015 | Strahl | |
| 9,155,891 B2 * | 10/2015 | Archer | A61N 1/36125 |
| 9,155,892 B2 | 10/2015 | Parker et al. | |
| 9,174,051 B2 | 11/2015 | Marnfeldt et al. | |
| 9,248,274 B2 | 2/2016 | Troosters et al. | |
| 9,248,279 B2 | 2/2016 | Chen et al. | |
| 9,259,574 B2 | 2/2016 | Aghassian et al. | |
| 9,265,431 B2 | 2/2016 | Hincapie Ordonez et al. | |
| 9,302,112 B2 | 4/2016 | Bornzin et al. | |
| 9,314,632 B2 | 4/2016 | Marnfeldt et al. | |
| 9,381,356 B2 | 7/2016 | Parker et al. | |
| 9,386,934 B2 | 7/2016 | Parker et al. | |
| 9,403,013 B2 | 8/2016 | Walker et al. | |
| 9,409,020 B2 | 8/2016 | Parker | |
| 9,468,765 B2 | 10/2016 | Archer | |
| 9,526,897 B2 | 12/2016 | Chen et al. | |
| 9,533,148 B2 | 1/2017 | Carcieri et al. | |
| 9,604,061 B2 | 3/2017 | Archer | |
| 9,656,084 B2 | 5/2017 | McDonald et al. | |
| 9,724,508 B2 | 8/2017 | Lamont et al. | |
| 9,731,116 B2 | 8/2017 | Chen | |
| 9,872,990 B2 | 1/2018 | Parker et al. | |
| 9,974,455 B2 | 5/2018 | Parker et al. | |
| 10,076,667 B2 | 9/2018 | Kaula et al. | |
| 2002/0156513 A1 | 10/2002 | Borkan | |
| 2005/0090756 A1 | 4/2005 | Wolf et al. | |
| 2005/0246004 A1 | 11/2005 | Cameron et al. | |
| 2006/0271118 A1 | 11/2006 | Libbus et al. | |
| 2008/0077039 A1 * | 3/2008 | Donnett | A61B 5/4094 600/544 |
| 2008/0146894 A1 | 6/2008 | Bulkes et al. | |
| 2012/0092031 A1 * | 4/2012 | Shi | A61N 1/36125 607/66 |
| 2012/0095519 A1 | 4/2012 | Parramon et al. | |
| 2012/0095529 A1 | 4/2012 | Parramon et al. | |
| 2013/0289665 A1 | 10/2013 | Marnfeldt et al. | |
| 2014/0194772 A1 | 7/2014 | Single et al. | |
| 2014/0236042 A1 | 8/2014 | Parker et al. | |
| 2014/0296737 A1 | 10/2014 | Parker et al. | |
| 2015/0080982 A1 | 3/2015 | Funderburk | |
| 2015/0157861 A1 | 6/2015 | Aghassian | |
| 2015/0231402 A1 | 8/2015 | Aghassian | |
| 2015/0282725 A1 | 10/2015 | Single et al. | |
| 2015/0313487 A1 | 11/2015 | Single et al. | |
| 2015/0360038 A1 | 12/2015 | Zottola et al. | |
| 2016/0166164 A1 | 6/2016 | Obradovic et al. | |
| 2016/0287126 A1 | 10/2016 | Parker et al. | |
| 2016/0287182 A1 | 10/2016 | Single et al. | |
| 2017/0049345 A1 | 2/2017 | Single et al. | |
| 2017/0071490 A1 | 3/2017 | Parker et al. | |
| 2017/0135624 A1 | 5/2017 | Parker et al. | |
| 2017/0216587 A1 | 8/2017 | Parker et al. | |
| 2017/0216600 A1 | 8/2017 | Feldman et al. | |
| 2017/0296823 A1 | 10/2017 | Hershey et al. | |
| 2017/0361101 A1 | 12/2017 | Single et al. | |
| 2018/0071520 A1 | 3/2018 | Weerakoon et al. | |
| 2018/0071527 A1 | 3/2018 | Feldman et al. | |
| 2018/0110987 A1 | 4/2018 | Parker et al. | |
| 2018/0117335 A1 | 5/2018 | Parker et al. | |
| 2018/0132747 A1 | 5/2018 | Parker et al. | |
| 2018/0132760 A1 | 5/2018 | Parker et al. | |
| 2018/0133459 A1 | 5/2018 | Parker et al. | |
| 2018/0140831 A1 | 5/2018 | Feldman et al. | |
| 2018/0228391 A1 | 8/2018 | Parker et al. | |
| 2018/0228547 A1 | 8/2018 | Parker et al. | |
| 2018/0256052 A1 | 9/2018 | Parker et al. | |
| 2019/0083796 A1 | 3/2019 | Weerakoon et al. | |
| 2019/0099602 A1 | 4/2019 | Esteller et al. | |
| 2019/0175915 A1 | 6/2019 | Brill et al. | |
| 2019/0209844 A1 | 7/2019 | Esteller et al. | |
| 2019/0275331 A1 | 9/2019 | Zhu et al. | |
| 2019/0290900 A1 | 9/2019 | Esteller et al. | |
| 2019/0299006 A1 | 10/2019 | Marnfeldt et al. | |
| 2019/0366094 A1 | 12/2019 | Esteller et al. | |
| 2020/0155019 A1 | 5/2020 | Esteller et al. | |
| 2020/0305745 A1 | 10/2020 | Wagenbach et al. | |

FOREIGN PATENT DOCUMENTS

| | | |
|---|---|---|
| WO | 2013/109603 | 7/2013 |
| WO | 2015/077362 | 5/2015 |
| WO | 2017/100866 | 6/2017 |
| WO | 2017/173493 | 10/2017 |
| WO | 2017/210352 | 12/2017 |
| WO | 2017/219096 | 12/2017 |

OTHER PUBLICATIONS

M. Moffit et al., A Novel 3-Dimensional Algorithm for Model-Based Programming in Spinal Cord Stimuation (SCS): Illumina-3D™, presentation (2013).

M. Hughes, "Fundamentals of Clinical ECAP Measures in Cochlear Implants: Part 1: Use of the ECAP in Speech Processor Program-

(56) References Cited

OTHER PUBLICATIONS ming (2nd Ed.)," Audiology Online (Nov. 8, 2010) (http://www.audiologyonline.com/articles/fundamentalsclinicalecapmeasuresin846).

I. Akhoun et al., "Electrically evoked compound action potential artifact rejection by independent component analysis: Technique validation," Hearing Research 302, pp. 60-73 (2013).

J. Rubinstein et al., "Pseudospontaneous activity: stochastic independence of auditory nerve fibers with electrical stimulation," Hear Res., 127(1-2), pp. 108-118 (1999) (abstract only).

J. Paz, "Physiological Midline Mapping Based on Spinal Cord Stimulation (SCS) Response Using the 32-Contact Paddle Lead," 19$^{th}$ NANS Annual Meeting (Dec. 13-15, 2015).

E.L. Air et al., "Electrophysiologic Monitoring for Placement of Laminectomy Leads for Spinal Cord Stimulation Under General Anesthesia," Neuromodulation: Technology at the Neural Interface, vol. 15(6), pp. 573-580 (2012).

J.L. Shils et al., "Intraoperative Neurophysiologic Methods for Spinal Cord Stimulator Placement Under General Anesthesia," Neuromodulation: Technology at the Neural Interface, vol. 15(6), pp. 560-572 (2012).

A. Taghva et al., "Intraoperative Electromyography as an Adjunct to Sacral Neuromodulation for Chronic Pelvic Pain," Neuromodulation: Technology at the Neural Interface, vol. 18(1), pp. 62-66 (2015).

\* cited by examiner

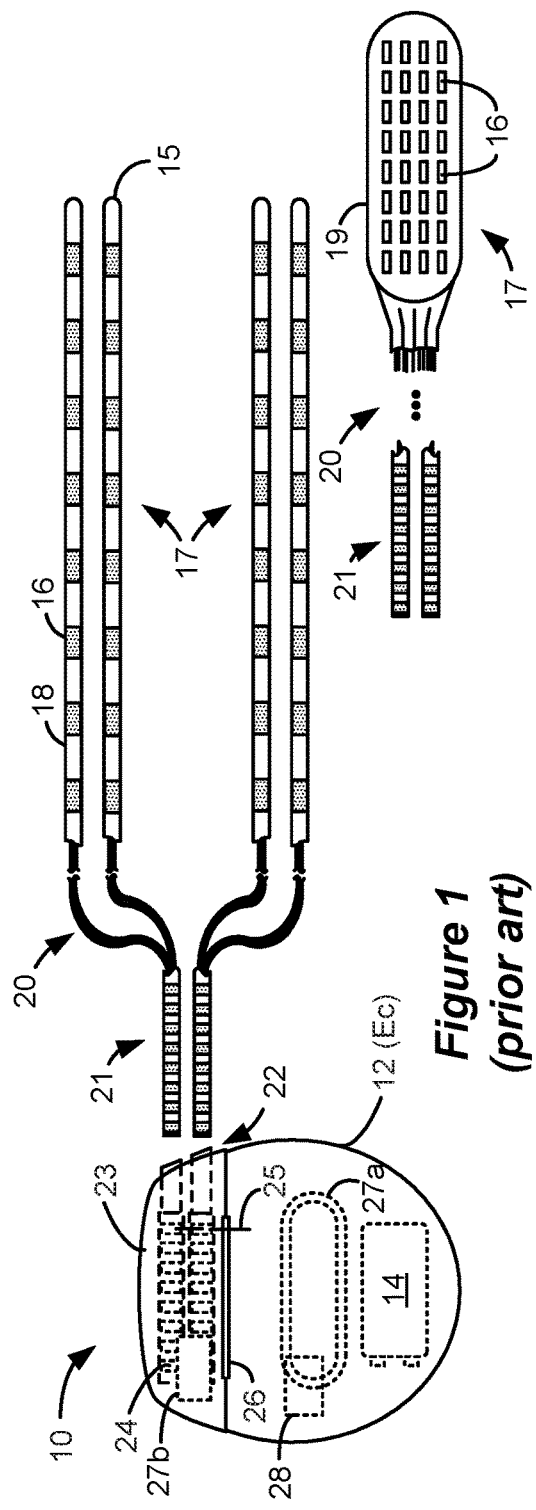
*Figure 1 (prior art)*
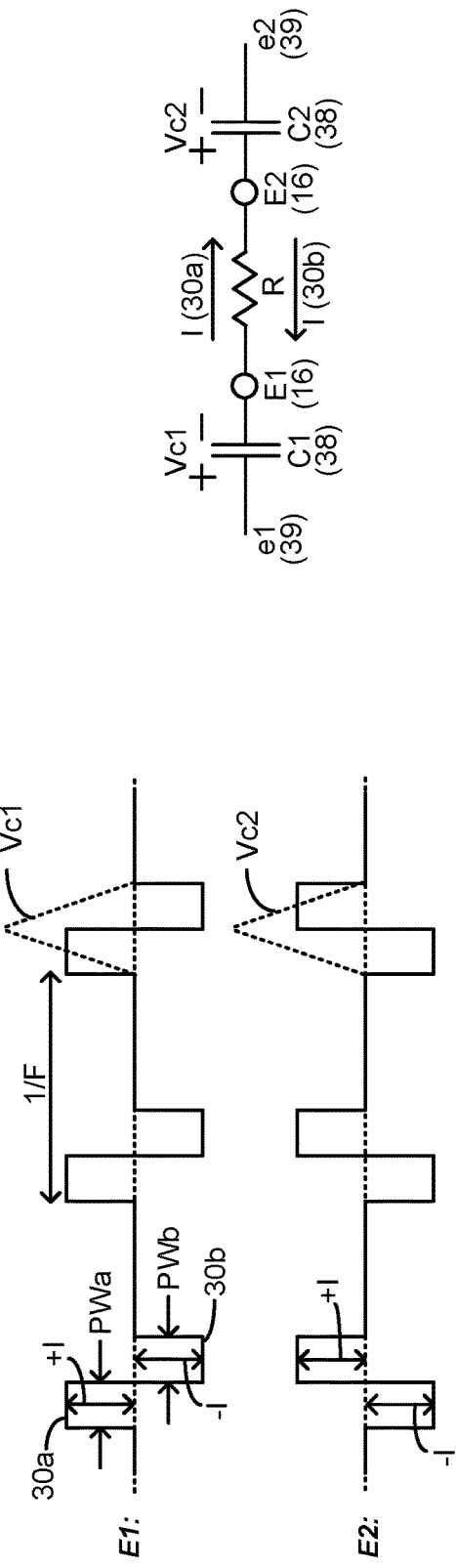
*Figure 2A (prior art)*
*Figure 2B (prior art)*

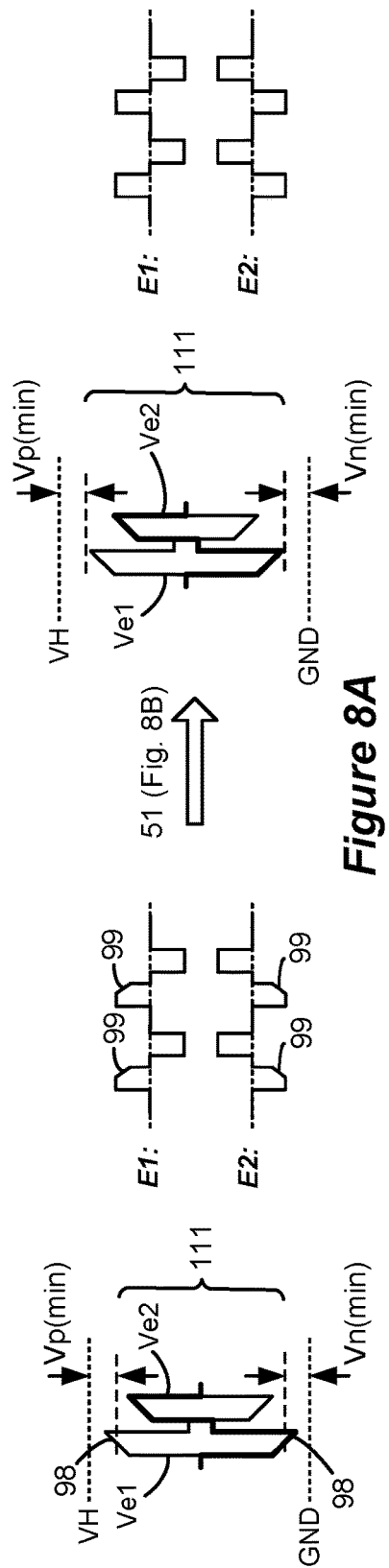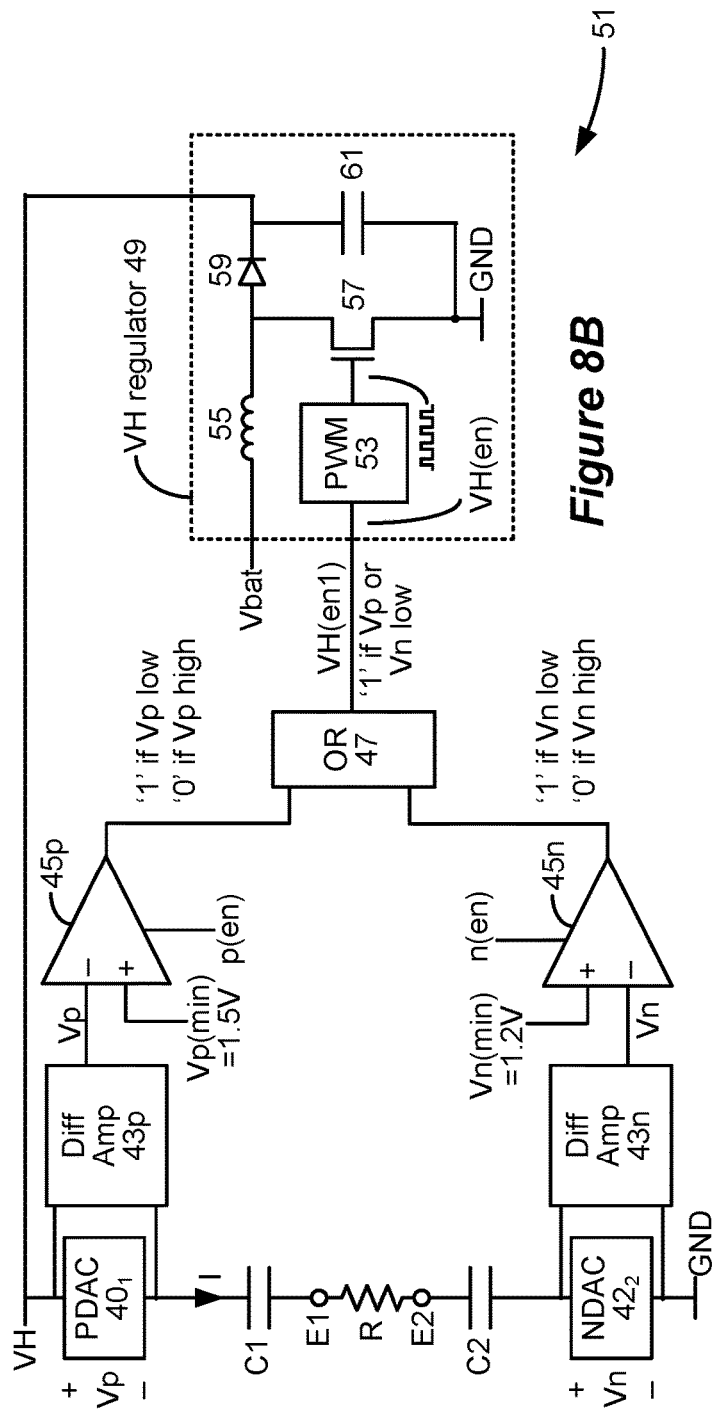
Figure 8A
Figure 8B

*R1 > R2:*

*R1 < R2:*

CIRCUITRY TO ASSIST WITH NEURAL SENSING IN AN IMPLANTABLE STIMULATOR DEVICE

CROSS REFERENCE TO RELATED APPLICATIONS

This is a continuation application of U.S. patent application Ser. No. 18/171,597, filed Feb. 20, 2023 (now U.S. Pat. No. 11,931,579), which is a continuation application of U.S. patent Application Ser. No. 17/323,748, filed May 18, 2021 (now U.S. Pat. No. 11,607,549), which is a continuation application of U.S. patent application Ser. No. 16/282,137, filed Feb. 21, 2019 (now U.S. Pat. No. 11,040,202), which is a non-provisional application of U.S. Provisional Patent Application Ser. No. 62/650,844, filed Mar. 30, 2018. Priority is claimed to these applications, and they are incorporated herein by reference in their entireties.

FIELD OF THE INVENTION

This application relates to Implantable Medical Devices (IMDs), and more specifically to circuitry to assist with sensing in an implantable stimulator device.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application specific and therefore can vary. The conductive case 12 can also comprise an electrode (Ec). In a SCS application, the electrode lead(s) are typically implanted in the spinal column proximate to the dura in a patient's spinal cord, preferably spanning left and right of the patient's spinal column. The proximal contacts 21 are tunneled through the patient's tissue to a distant location such as the buttocks where the IPG case 12 is implanted, at which point they are coupled to the lead connectors 22. In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. The goal of SCS therapy is to provide electrical stimulation from the electrodes 16 to alleviate a patient's symptoms, such as chronic back pain.

IPG 10 can include an antenna 27a allowing it to communicate bi-directionally with a number of external devices discussed subsequently. Antenna 27a as shown comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b. In FIG. 1, RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth, Zigbee, WiFi, MICS, and the like.

Stimulation in IPG 10 is typically provided by pulses each of which may include a number of phases such as 30a and 30b, as shown in the example of FIG. 2A. Stimulation parameters typically include amplitude (current I, although a voltage amplitude V can also be used); frequency (F); pulse width (PW) of the pulses or of its individual phases such as 30a and 30b; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E1 has been selected as an anode (during its first phase 30a), and thus provides pulses which source a positive current of amplitude +I to the tissue. Electrode E2 has been selected as a cathode (again during first phase 30a), and thus provides pulses which sink a corresponding negative current of amplitude −I from the tissue. This is an example of bipolar stimulation, in which only two lead-based electrodes are used to provide stimulation to the tissue (one anode, one cathode). However, more than one electrode may be selected to act as an anode at a given time, and more than one electrode may be selected to act as a cathode at a given time.

IPG 10 as mentioned includes stimulation circuitry 28 to form prescribed stimulation at a patient's tissue. FIG. 3 shows an example of stimulation circuitry 28, which includes one or more current source circuits 40 and one or more current sink circuits $42_i$. The sources and sinks $40_i$ and $42_i$ can comprise Digital-to-Analog converters (DACs), and may be referred to as PDACs $40_i$ and NDACs $42_i$ in accordance with the Positive (sourced, anodic) and Negative (sunk, cathodic) currents they respectively issue. In the example shown, a NDAC/PDAC $40_i/42_i$ pair is dedicated (hardwired) to a particular electrode node ei 39. Each electrode node ei 39 is connected to an electrode Ei 16 via a DC-blocking capacitor Ci 38, for the reasons explained below. The stimulation circuitry 28 in this example also supports selection of the conductive case 12 as an electrode (Ec 12), which case electrode is typically selected for monopolar stimulation. PDACs $40_i$ and NDACs $42_i$ can also comprise voltage sources.

Proper control of the PDACs $40_i$ and NDACs $42_i$ allows any of the electrodes 16 to act as anodes or cathodes to create a current through a patient's tissue, R, hopefully with good therapeutic effect. In the example shown, electrode E1 has been selected as an anode electrode to source current to the tissue R and E2 as a cathode electrode to sink current from the tissue R. Thus PDAC $40_1$ and NDAC $42_2$ are activated and digitally programmed to produce the desired current, I, with the correct timing (e.g., in accordance with the prescribed frequency F and pulse widths PWa and PWb). Power for the stimulation circuitry 28 is provided by a compliance voltage VH, as described in further detail in U.S. Patent Application Publication 2013/0289665. As shown the compliance voltage may be coupled to the source circuitry (e.g., the PDAC(s)), while ground may be coupled to the sink circuitry (e.g., the NDAC(s)), such that the stimulation circuitry is coupled to and powered between the compliance voltage and ground. More than one anode electrode and more than one cathode electrode may be selected at one time, and thus current can flow through the tissue R between two or more of the electrodes 16.

Other stimulation circuitries 28 can also be used in the IPG 10. In an example not shown, a switching matrix can intervene between the one or more PDACs $40_i$ and the electrode nodes ei 39, and between the one or more NDACs $42_i$ and the electrode nodes. Switching matrices allows one or more of the PDACs or one or more of the NDACs to be connected to one or more anode electrode nodes at a given time. Various examples of stimulation circuitries can be found in U.S. Pat. Nos. 6,181,969, 8,606,362, 8,620,436, 10,912,942, and U.S. Patent Application Publication 2018/0071520.

Much of the stimulation circuitry 28 of FIG. 3, including the PDACs $40_i$ and NDACs $42_i$, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519. As explained in these references, ASIC(s) may also contain other circuitry useful in the IPG 10, such as telemetry circuitry (for interfacing off chip with telemetry antennas 27a and/or 27b), circuitry for generating the compliance voltage VH, various measurement circuits, etc.

Also shown in FIG. 3 are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28, and also generally comprise part of the IPG's charge balancing mechanism. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861.

Referring again to FIG. 2A, the stimulation pulses as shown are biphasic, with each pulse comprising a first phase 30a followed thereafter by a second phase 30b of opposite polarity. Biphasic pulses are useful to actively recover any charge that might be stored on capacitive elements in the electrode current paths, such as on the DC-blocking capacitors 38. Charge recovery is shown with reference to both FIGS. 2A and 2B. During the first pulse phase 30a, charge will (primarily) build up across the DC-blockings capacitors C1 and C2 associated with the electrodes E1 and E2 used to produce the current, giving rise to voltages Vc1 and Vc2 ($I=C*dV/dt$). During the second pulse phase 30b, when the polarity of the current I is reversed at the selected electrodes E1 and E2, the stored charge on capacitors C1 and C2 is recovered, and thus voltages Vc1 and Vc2 hopefully return to 0V at the end the second pulse phase 30b.

To recover all charge by the end of the second pulse phase 30b of each pulse (Vc1=Vc2=0V), the first and second phases 30a and 30b are charged balanced at each electrode, with the phases comprising an equal amount of charge but of the opposite polarity. In the example shown, such charge balancing is achieved by using the same pulse width (PWa=PWb) and the same amplitude (|+I|=|−I|) for each of the pulse phases 30a and 30b. However, the pulse phases 30a and 30b may also be charged balance if the product of the amplitude and pulse widths of the two phases 30a and 30b are equal, as is known.

FIG. 4 shows various external devices that can wirelessly communicate data with the IPG 10, including a patient, hand-held external controller 60, and a clinician programmer 70. Both of devices 60 and 70 can be used to wirelessly transmit a stimulation program to the IPG 10—that is, to program its stimulation circuitry 28 to produce stimulation with desired amplitudes and timings as described earlier. Both devices 60 and 70 may also be used to adjust one or more stimulation parameters of a stimulation program that the IPG 10 is currently executing. Devices 60 and 70 may also wirelessly receive information from the IPG 10, such as various status information, etc. Devices 60 and 70 may additionally communicate with an External Trial Stimulator (ETS) which is used to mimic operation of the IPG 10 during a trial period and prior to the IPG's implantation, as explained in U.S. Pat. Nos. 9,724,508 and 9,259,574.

External controller 60 can be as described in U.S. Patent Application Publication 2015/0080982 for example, and may comprise a controller dedicated to work with the IPG 10. External controller 60 may also comprise a general purpose mobile electronics device such as a mobile phone which has been programmed with a Medical Device Application (MDA) allowing it to work as a wireless controller for the IPG 10, as described in U.S. Patent Application Publication 2015/0231402. External controller 60 includes a user interface, preferably including means for entering commands (e.g., buttons or selectable graphical icons) and a display 62. The external controller 60's user interface enables a patient to adjust stimulation parameters, although it may have limited functionality when compared to the more-powerful clinician programmer 70, described shortly.

The external controller 60 can have one or more antennas capable of communicating with the IPG 10. For example, the external controller 60 can have a near-field magnetic-induction coil antenna 64a capable of wirelessly communicating with the coil antenna 27a in the IPG 10. The external controller 60 can also have a far-field RF antenna 64b capable of wirelessly communicating with the RF antenna 27b in the IPG 10.

Clinician programmer 70 is described further in U.S. Patent Application Publication 2015/0360038, and can comprise a computing device 72, such as a desktop, laptop, or notebook computer, a tablet, a mobile smart phone, a Personal Data Assistant (PDA)-type mobile computing device, etc. In FIG. 4, computing device 72 is shown as a laptop computer that includes typical computer user interface means such as a screen 74, a mouse, a keyboard, speakers, a stylus, a printer, etc., not all of which are shown for convenience. Also shown in FIG. 4 are accessory devices for the clinician programmer 70 that are usually specific to its operation as a stimulation controller, such as a communication "wand" 76 coupleable to suitable ports on the computing device 72, such as USB ports 79 for example.

The antenna used in the clinician programmer 70 to communicate with the IPG 10 can depend on the type of antennas included in the IPG 10. If the patient's IPG 10 includes a coil antenna 27a, wand 76 can likewise include a coil antenna 80a to establish near-filed magnetic-induction communications at small distances. In this instance, the wand 76 may be affixed in close proximity to the patient, such as by placing the wand 76 in a belt or holster wearable by the patient and proximate to the patient's IPG 10. If the IPG 10 includes an RF antenna 27b, the wand 76, the computing device 72, or both, can likewise include an RF antenna 80b to establish communication with the IPG 10 at larger distances. The clinician programmer 70 can also communicate with other devices and networks, such as the Internet, either wirelessly or via a wired link provided at an Ethernet or network port.

To program stimulation programs or parameters for the IPG 10, the clinician interfaces with a clinician programmer graphical user interface (GUI) 82 provided on the display 74 of the computing device 72. As one skilled in the art understands, the GUI 82 can be rendered by execution of clinician programmer software 84 stored in the computing device 72, which software may be stored in the device's non-volatile memory 86. Execution of the clinician programmer software 84 in the computing device 72 can be facilitated by control circuitry 88 such as one or more microprocessors, microcomputers, FPGAs, DSPs, other digital logic structures, etc., which are capable of executing programs in a computing device, and which may comprise their own memories. Such control circuitry 88, in addition to executing the clinician programmer software 84 and rendering the GUI 82, can also enable communications via antennas 80a or 80b to communicate stimulation parameters chosen through the GUI 82 to the patient's IPG 10.

The user interface of the external controller 60 may provide similar functionality because the external controller 60 can include similar hardware and software programming as the clinician programmer. For example, the external controller 60 includes control circuitry 66 similar to the control circuitry 88 in the clinician programmer 70, and may similarly be programmed with external controller software stored in device memory.

SUMMARY

An implantable stimulator device is disclosed, which may comprise: a plurality of electrode nodes, each electrode node configured to be coupled to one of a plurality of electrodes configured to contact a patient's tissue; a case configured for implantation in the patient's tissue, where the case contains stimulation circuitry configured to provide pulses at at least two of the electrode nodes to create a stimulation current through the patient's tissue; and a capacitance configured to be coupled between at least one of the plurality of electrodes and a first reference voltage produced inside the case when the stimulation circuitry is providing the pulses to the at least two electrode nodes, where the capacitance is configured to provide a common mode voltage to the tissue at the at least one electrode.

The case may be conductive, and the conductive case may comprise one of the plurality of electrodes. The conductive case may comprise the at least one electrode.

The at least one electrode may be configured to be selectable from the plurality of electrodes.

The implantable stimulator device may further comprise a resistor in parallel with the capacitance.

The capacitance may comprise one or more capacitors.

Each electrode node may be coupled to an electrode through a DC-blocking capacitor.

The stimulation circuitry may be further configured to provide pulses to the at least one electrode, where the capacitance is configured to be uncoupled between the at least one electrode and the first reference voltage when the stimulation circuitry is providing the pulses to the at least one electrode.

The implantable stimulator device may further comprise at least one implantable lead, where the electrodes are located on the lead. The implantable stimulator device may also further comprise a switch configured to couple the capacitance to the first reference voltage. The implantable stimulator device may also further comprise a voltage source configured to produce the first reference voltage.

The stimulation circuitry may be configured to be powered by a compliance voltage. The stimulation may comprise source circuitry configured to source a current to at least one of the two electrodes, and sink circuitry configured to sink a current from a different at least one of the two electrodes. The compliance voltage may be coupled to the source circuitry, and a ground may be coupled to the current sink circuitry. The first reference voltage may be between the compliance voltage and a ground, or may be configured to scale with the compliance voltage.

The implantable stimulator device may further comprise an amplifier configured to produce the first reference voltage. The amplifier may comprise an operational transconductance amplifier. The amplifier may comprise a first input and a second input, and may be configured as a follower in which the first reference voltage is provided to the first input, and where a second reference voltage is provided to the second input. The implantable stimulator device may further comprise a voltage source configured to produce the second reference voltage. The stimulation circuitry may be configured to be powered by a compliance voltage. The second reference voltage may be between the compliance voltage and a ground, or may be configured to scale with the compliance voltage. The amplifier may be configured to maintain the first reference voltage equal to the second reference voltage if a current through the capacitance is between a minimum and maximum output current of the amplifier.

The implantable stimulator device may further comprise logic circuitry configured to determine whether the first reference voltage exceeds a first threshold or falls below a second threshold. The implantable stimulator device may further comprise control circuitry configured to receive at least one indication that the first reference voltage has exceeded the first threshold or has fallen below the second threshold. The control circuitry may be configured in response to the at least one indication to issue an enable signal indicating when a neural response in the tissue in response to the stimulation current can be sensed at at least one of the plurality of electrode nodes. The stimulation circuitry may be powered by a compliance voltage, where the control circuitry is configured in response to the at least one indication to issue an enable signal indicating when the compliance voltage should be increased.

The implantable stimulator device may further comprise at least one sense amplifier configured to sense a neural response in the tissue in response to the stimulation current when the capacitance is configured to provide the common mode voltage to the tissue at the at least one electrode. The at least one sense amplifier may comprise a first input and a second input, where the at least one sense amplifier is configured to receive one of the electrode nodes at its first input. The one electrode node received at the first input may not comprise one of the at least two of the electrode nodes. The at least one sense amplifier may be configured to receive the common mode voltage at its second input. The at least one sense amplifier may also be configured to receive another one of the electrode nodes at its second input to differentially sense the neural response between the one electrode node and the another electrode node. The implantable stimulator device may further comprise control circuitry configured to receive an output of the at least one sense amplifier and to assess at least one parameter of the sensed neural response.

BRIEF DESCRIPTION OF THE DRAWINGS

FIG. 1 shows an Implantable Pulse Generator (IPG), in accordance with the prior art.

FIGS. 2A and 2B show an example of stimulation pulses producible by the IPG, in accordance with the prior art.

FIGS. 8A and 8B show the problem of insufficient compliance voltage producing stimulation pulses that are loaded, and show circuitry for adjusting the compliance voltage to prevent loading in a closed loop fashion.

DETAILED DESCRIPTION

An increasingly interesting development in pulse generator systems, and in Spinal Cord Stimulator (SCS) pulse generator systems specifically, is the addition of sensing capability to complement the stimulation that such systems provide. For example, and as explained in U.S. Patent Application Publication 2017/0296823, it can be beneficial to sense a neural response in neural tissue that has received stimulation from an SCS pulse generator.

Figure 5:
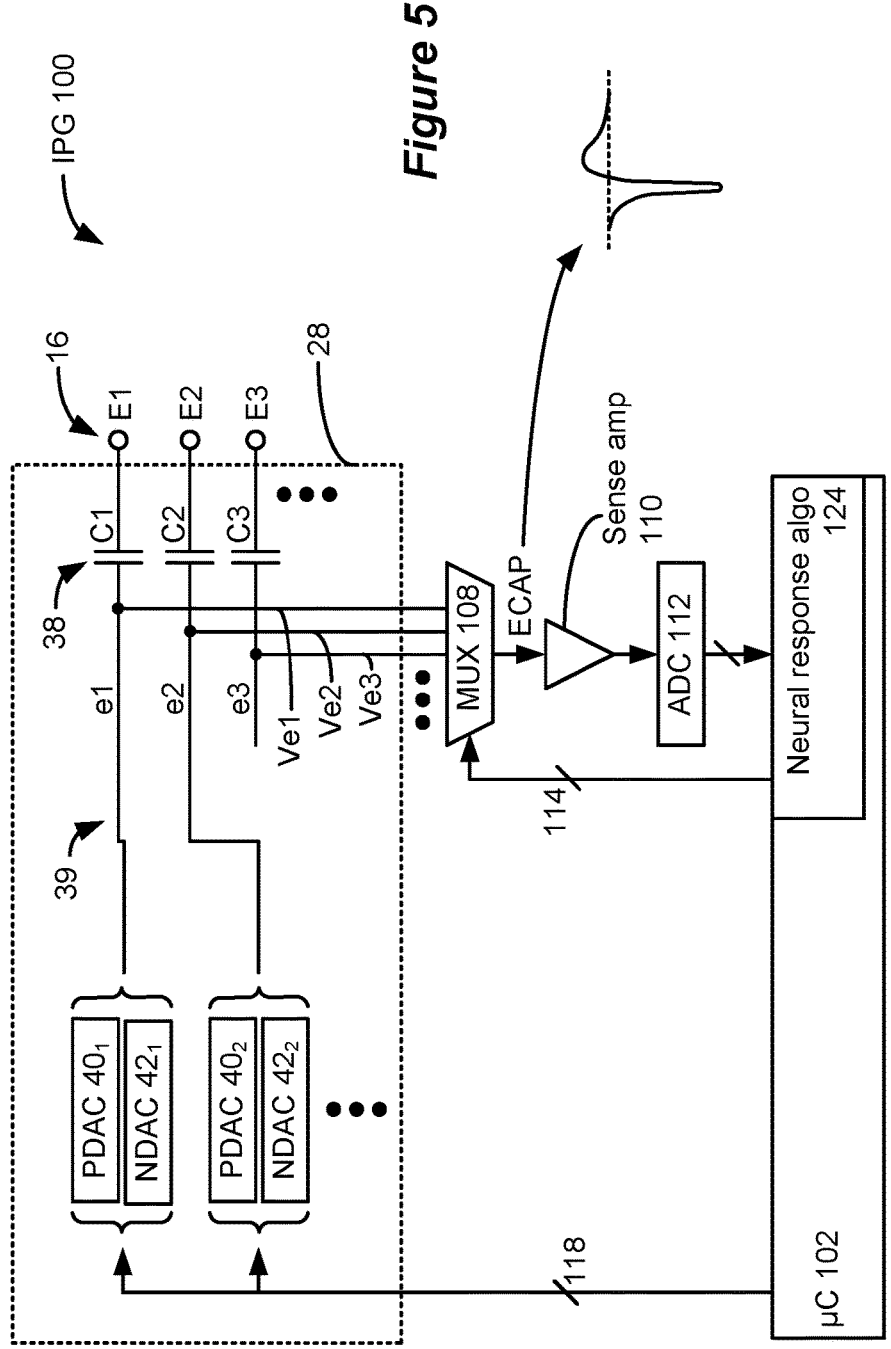
FIG. 5 shows an improved IPG having neural response sensing, and the ability to adjust stimulation dependent on such sensing.

FIG. 5 shows circuitry for an SCS IPG 100 having neural response sensing capability. The IPG 100 includes control circuitry 102, which may comprise a microcontroller for example, such as Part Number MSP430, manufactured by Texas Instruments, which is described in data sheets at http://www.ti.com/lsds/ti/microcontroller/16-bit_msp430/overview.page?DCMP=MCU_other&HQS=msp430. Other types of control circuitry may be used in lieu of a microcontroller as well, such as microprocessors, FPGAs, DSPs, or combinations of these, etc.

Control circuitry 102 may also be formed in whole or in part in one or more Application Specific Integrated Circuits (ASICs) in the IPG 100 as described earlier, which ASIC(s) may additionally include the other circuitry shown in FIG. 5.

Figure 3:
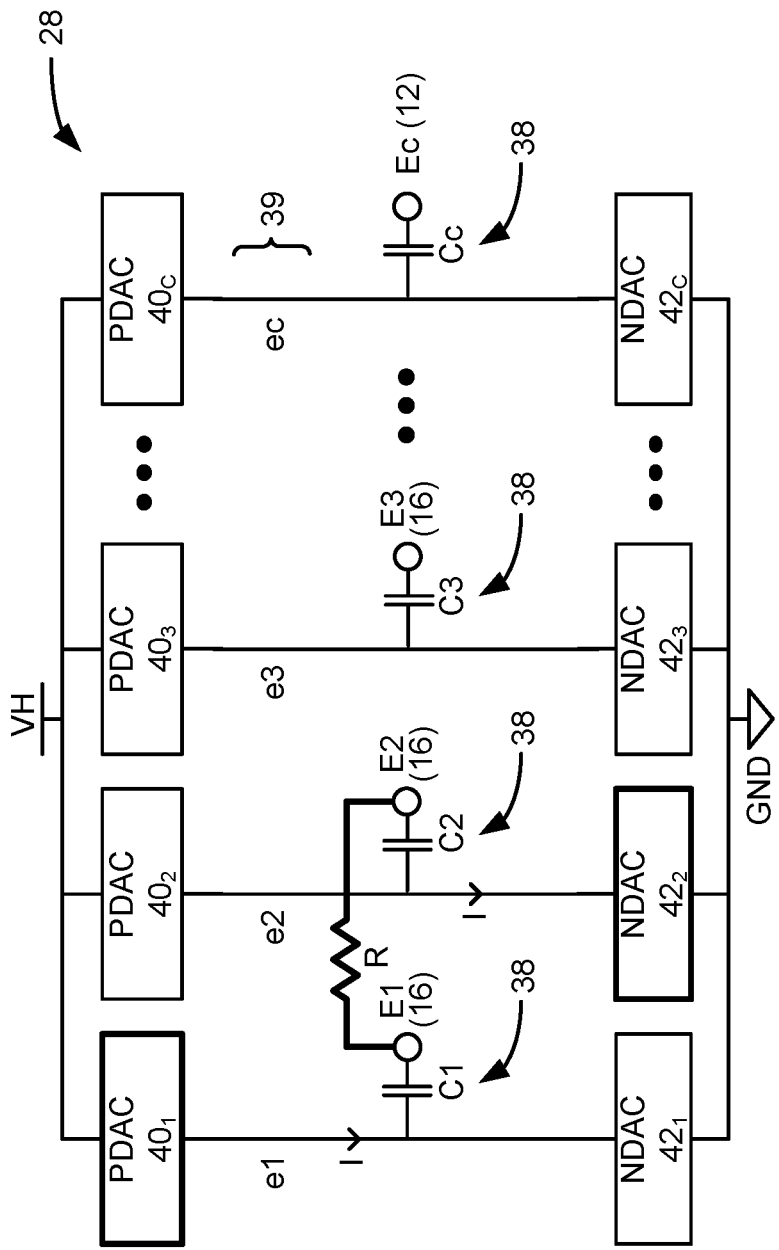
FIG. 3 shows stimulation circuitry useable in the IPG, in accordance with the prior art.

FIG. 5 includes the stimulation circuitry 28 described earlier (FIG. 3), including one or more DACs (PDACs $40_i$ and NDACs $42_i$). A bus 118 provides digital control signals to the DACs to produce currents or voltages of prescribed amplitudes and with the correct timing at the electrodes selected for stimulation. The electrode current paths to the electrodes 16 include the DC-blocking capacitors 38 described earlier.

The control circuitry 102 is programmed with a neural response algorithm 124 to evaluate a neural response of neurons that fire (are recruited) by the stimulation that the IPG 100 provides.

Figure 6:
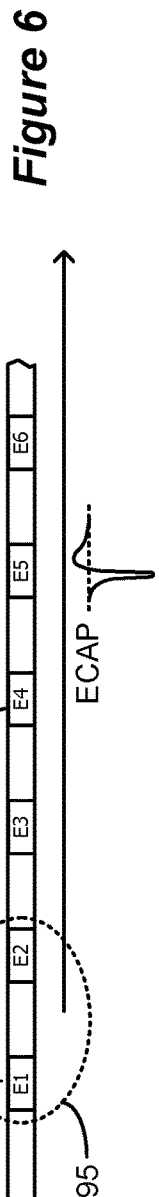
FIG. 6 shows stimulation producing a neural response, and the sensing of that neural response at at least one electrode of the IPG.

One such neural response depicted in FIGS. 5 and 6 is an Evoked Compound Action Potential, or "ECAP," although other types of neural responses also exist and can be sensed by the IPG 100. As its name implies, an ECAP comprises a compound (summation) of various action potentials issued from a plurality of recruited neurons, and its amplitude and shape varies depending on the number and type of neural fibers that are firing. Generally speaking, an ECAP can vary between tens of microVolts to tens of milliVolts. The neural response algorithm 124 assesses the ECAP and can, for example, adjust the stimulation program in a closed loop fashion to try and adjust the amplitude or shape of the resulting ECAP.

Figure 4:
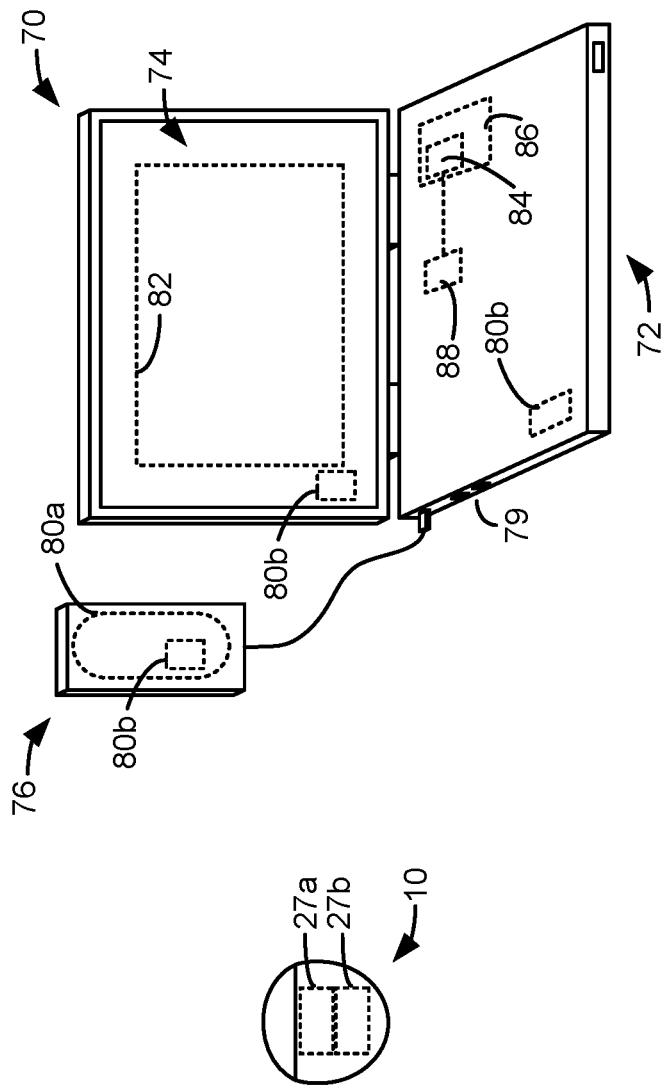
FIG. 4 shows various external devices capable of communicating with and programming stimulation in an IPG, in accordance with the prior art.
Figure 4:
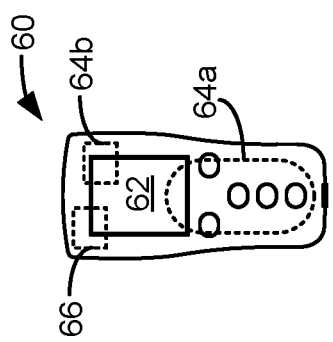

The control circuitry 102 and/or the neural response algorithm 124 can also enable one or more sense electrodes (S) to sense the ECAP, either automatically or based on a user selection of the sense electrode(s) as entered into an external device (see FIG. 4). As shown in FIG. 6, the ECAP will be initiated upon stimulation of neural fibers in a recruited neural population 95 proximate to the electrodes chosen for stimulation (e.g., E1 and E2), and will move through the patient's tissue via neural conduction. In the simple example of FIG. 6, electrode E6 is chosen as a sense electrode S, and thus this electrode will detect the ECAP as it moves past. The speed at which the ECAP moves depends on the several factors, and is variable.

To assist with selection of the sensing electrode(s), and referring again to FIG. 5, each electrode node ei 39 is made coupleable to at least one sense amp 110. In this example, for simplicity, all of the electrode nodes are shown as sharing a single sense amp 110. Thus, any one sensing electrode (e.g., electrode node e6) can be coupled to the sense amp 110 (e.g., Ve6) at a given time per multiplexer 108, as controlled by bus 114. However, although not shown, each electrode node can also be coupleable to its own dedicated sense amp 110. ECAP sensing can also involve differential sensing of the ECAP at more than one electrode (e.g., at electrodes E5 and E6), and thus two electrode nodes (e.g., Ve5 and Ve6) can be input to a differential sense amp 110; this is explained later with reference to FIG. 14B, but isn't shown in FIGS. 5 and 6 for simplicity. After the ECAP is sensed, the analog waveform comprising the ECAP is preferably converted to digital signals by an Analog-to-Digital converter 112, which may also reside within the control circuitry 102. The neural response algorithm 124 can then assess the amplitude and shape of the ECAP, and if necessary make adjustments to stimulation via bus 118 to try and adjust resulting future ECAPs so that they have desired amplitudes or shapes.

The sensing electrode(s) S may be distant from the active electrodes chosen to provide stimulation so that voltages created in the tissue during stimulation (stimulation artifacts) will less affect sensing at the sensing electrode. Nonetheless, because the duration (e.g., PWa and PWb) and frequency (F) of the stimulation pulses and the conduction speed of neural responses are variable, it may be inevitable that stimulation-related voltages are present at the sensing electrode(s) chosen. This can make sensing neural responses challenging. As noted, an ECAP can be as small as tens of microVolts. However, as explained further below, operation of the IPG can cause the voltage in the tissue to vary on the order of Volts. Sensing thus involves resolving a small signal neural response in the tissue that may be many orders of magnitudes smaller than the varying background voltage of the tissue. It is difficult to design an amplifier such as sense amp(s) 110 to reliably perform the task of accurately sensing such a small signal while rejecting the background tissue voltage.

Figure 7A:
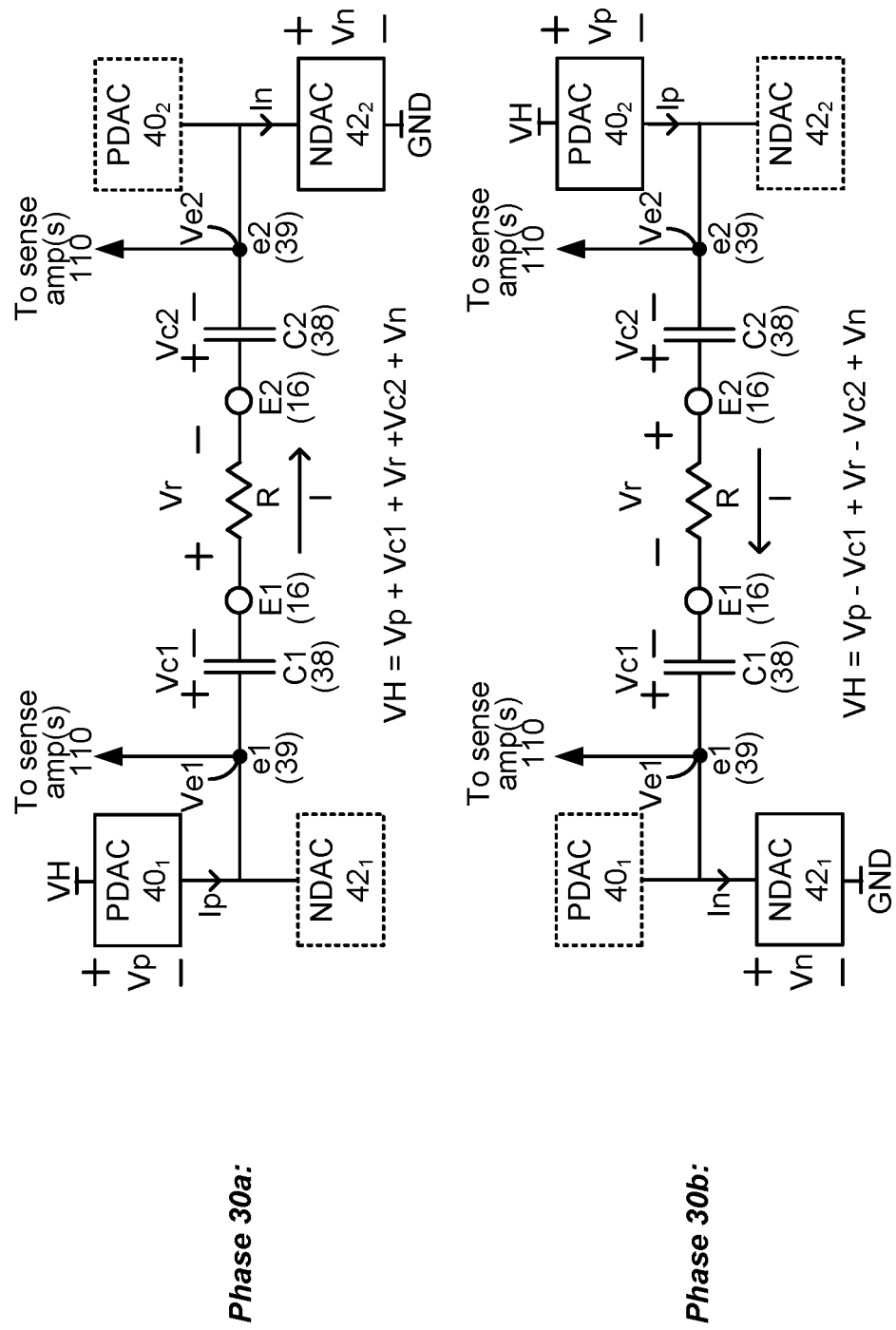
FIGS. 7A and 7B show the production of biphasic pulses at selected IPG electrodes, and shows the voltages formed at the selected electrode nodes.

Voltage variation in the tissue due to stimulation is first explained with reference to FIGS. 7A and 7B, which show stimulation occurring using biphasic pulses between electrodes E1 and E2 as described earlier. FIG. 7A shows how the stimulation circuitry 28 is biased when producing a current I through the tissue during the first phase 30a when current I travels from anode electrode E1 to cathode electrode E2, and during the second phase 30b when current I travels in the opposite direction from anode electrode E2 to cathode electrode E1. Note during the first phase 30a that a selected PDAC (e.g., PDAC $40_1$) sources current Ip to electrode node e1 while a selected NDAC (e.g., NDAC $42_2$) sinks current In from electrode node e2. During the second phase 30b, a selected PDAC (e.g., PDAC $40_2$) sources current Ip to electrode node e2 and a selected NDAC (e.g., NDAC $42_1$) sinks current In from electrode node e1. Ideally, Ip issued from the PDACs equals |In| issued by the NDACs, with both equaling the desired current I, although non-idealities may cause them to vary as discussed further below. The same PDAC and NDAC could also be used during the two phases 30a and 30b if switch matrices are used as part of the design of stimulation circuitry 28.

Figure 7B:
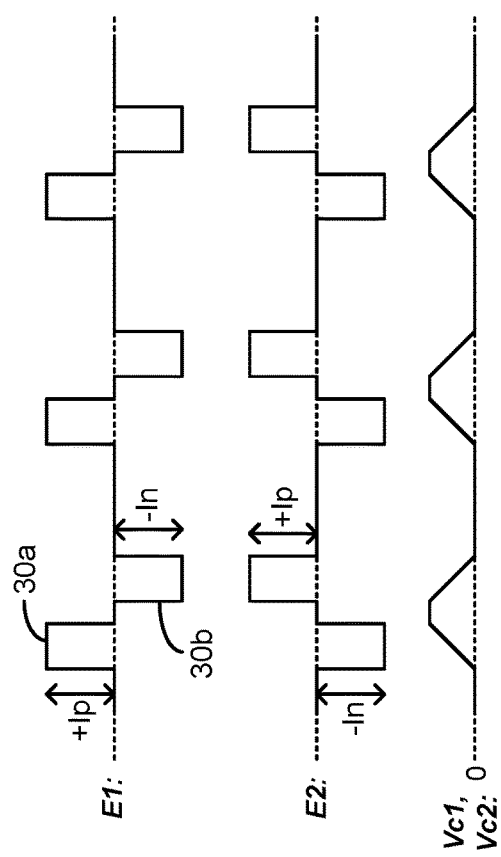

FIG. 7B shows various waveforms that are produced when biphasic current pulses are produced at electrodes E1 and E2. Providing a constant current I between the electrodes causes the DC-blocking capacitors 38 C1 and C2 to charge during the first pulse phases 30a, which causes the voltages across them Vc1 and Vc2 to increase (I=C*dV/dt). Because the second pulse phase 30b of opposite polarity is charge balanced with the first pulse phase 30a, Vc1 and Vc2 will decrease during the second pulse phases 30b and return (ideally) to zero at the end of the second pulse phase 30b, as explained earlier with reference to FIGS. 2A and 2B.

The bottom of FIG. 7B shows the voltages that are formed at the electrode nodes 39 e1 and e2 (Ve1 and Ve2) when producing the foregoing pulses. It is useful to review the voltages at the electrode nodes 39 ei rather than at the electrodes Ei 16 themselves because it is the voltages at the electrode nodes that are presented to the sense amp(s) 110 (FIG. 5) and hence used for neural response sensing. Even though Ve1 and Ve2 are formed at the same time, they are initially shown separately in FIG. 7B for simplicity, with the first waveform showing just Ve1 during a first pulse, and the second waveform showing just Ve2 during a second pulse. The third waveform shows Ve1 and Ve2 together during a third pulse.

The electrode node voltages Ve1 and Ve2 in FIG. 7B are shown with reference to the compliance voltage VH that as mentioned earlier (FIG. 3) is used to provide power to the DAC circuitry. All relevant voltage drops are shown, including the voltage drops across the tissue (Vr), the DC-blocking capacitors 39 (Vc1 and Vc2), and the selected PDACs and NDACs (Vp and Vn). As shown, Ve1 is initially higher than Ve2 because of the direction that the current is flowing during the first pulse phase 30a. Ve1 will increase and Ve2 will decrease during the first pulse phase 30a as the DC-blocking capacitors 38 charge (Vc1, Vc2). This also causes the voltage drops across the active PDAC (Vp) and NDAC (Vn) to decrease. During the second pulse phase 30b, the polarity of the current is reversed, and so Ve2 is now higher than Ve1. The voltages Vc2 and Vc2 decrease during the second pulse phase 30b as their stored charge is recovered, which causes Ve1 to decrease and Ve2 to increase, while Vp and Vn decrease.

Voltages Ve1 and Ve2 thus vary significantly during the issuance of the biphasic pulses, both because of the change in polarity of the current, and the charging and discharging of the DC-blocking capacitors 38. Such variation is indicative of variation of voltage in the tissue, which voltage will couple to at least some degree through the tissue to the electrodes that are used for sensing. Assume again that sensing is to occur at electrode E6—i.e., that sensed voltage Ve6 is presented to the sense amp(s) 110. Although it is complicated to calculate or graph given the complicated electrical environment of the tissue, voltages present at electrodes E1 and E2 will couple to electrode E6, and thus Ve6 will generally track Ve1 and/or Ve2 to some degree. (In this example, Ve6 would likely primarily track Ve2 because electrode E6 is closer to E2 than E1). In other words, any small signal neural response sensed at Ve6 will be riding on a large and varying background voltage, which as noted earlier makes sensing of the neural response difficult. As will be described further below, the addition of passive tissue biasing circuitry to the IPG 100 will provide a common mode voltage to the tissue which eases the sensing of small signal neural responses.

Before discussing such passive tissue biasing circuitry, it is useful to discuss how the compliance voltage VH can be adjusted in the IPG 100, because such adjustment can be implicated by the operation of the passive tissue biasing circuitry. Compliance voltage adjustment, and circumstances in which such adjustment is warranted, are shown in FIGS. 8A and 8B. When providing stimulation, the voltage drops Vp and Vn across the PDACs and NDACs are preferably held above minimum values Vp(min) and Vn(min), as explained in U.S. Pat. Nos. 7,444,181, 9,174,051 and 9,314,632. If Vp or Vn drop below these minimum values, the affected DAC, either the PDAC or NDAC, will become loaded and thus will be unable to produce its prescribed current Ip or In. This means that Ve1 and Ve2 preferably stay bounded within a region 111 between VH–Vp(min) and Vn(min). In the example of FIG. 8A, such bounding does not occur, because Ve2<Vn(min) and Ve1>VH–Vp(min) during part (98) of the first pulse phase 30*a*. This leads to loading (99) of the pulses because the PDAC(s) and NDAC(s) are unable to produce the prescribed currents of Ip and In.

While the compliance voltage may be constant, it is also preferably adjustable to address pulse loading, and FIG. 8B shows an example of compliance voltage measurement and generation circuitry 51 that can be used for this purpose. Generally speaking, compliance voltage measurement and generation circuitry 51 measures Vp and Vn across the active PDACs and NDACs, and adjusts the compliance voltage VH in a closed loop fashion to ensure that Vp does not fall below Vp(min) and that Vn does not fall below Vn(min), thus ensuring that the electrode node voltages Ve1 and Ve2 are bounded by region 111.

As shown, differential amplifiers 43*p* and 43*n* measure Vp and Vn across the active PDAC 40*i* and NDAC 42*j* during provision of the pulse (I). Note that FIG. 8B only shows measuring Vp and Vn across PDAC 40₁ and NDAC₄₂ during the first pulse phase 30*a*. Vp and Vn can also be measured across PDAC 40₂ and NDAC 42₁ during the second pulse phase 30*b* although this is not shown.

The Vp and Vn measurements are provided to negative inputs of comparators 45*p* and 45*n*. The comparators' positive inputs are provided with the minimum values of Vp and Vn (Vp(min) and Vn(min)) needed across the PDAC and NDAC to prevent loading. Vp(min) and Vn(min) can be different owing to differences in the construction of the PDACs and NDACs, and may for example be 1.5 V and 1.2V respectively. Vp(min) and Vn(min) can be provided by voltage generators such as bandgap voltage reference generators, although this detail isn't shown. Comparator 45*p* is enabled by signal p(en) to compare Vp and Vp(min) at a prescribed time, such as at the end of the first pulse phase 30*a* when Vc1 and Vc2 may be highest, and thus when Vp may be lowest. Comparator 45*n* is similarly enabled by signal n(en) to compare Vn and Vn(min) at the prescribed time when Vn may also be lowest. Comparators 45*p* and 45*n* will output a '1' if Vp is lower than Vp(min) or if Vn is lower than Vn(min). An OR gate 47 outputs a '1' if either Vp or Vn is low, which output signal comprises an enable signal VH(en1) to operate a compliance voltage regulator 49.

The compliance voltage (VH) regulator 49 is shown in this example as an inductor-based boost converter, but could also be implemented as a capacitor-based charge pump or other voltage-boosting circuitry. VH regulator 49 produces the compliance voltage VH from another typically-lower-voltage DC source in the IPG 100 such as the voltage of its battery 14 (FIG. 1), Vbat. When enabled by VH(en1) at input VH(en), a pulse width modulator 53 produces a square wave to a gating transistor 57, which periodically turns on the transistor 57 and causes current to flow from Vbat through an inductor 55. During off periods of the transistor 57, stored current in the inductor 55 is forced through a diode 59, and is stored on a storage capacitor 61 that holds the value of the compliance voltage VH. The diode 59 prevents the backflow of this current, and so over time, the voltage across the storage capacitor 61 increases, i.e., the compliance voltage VH, starts to build so long as VH(en1) continues to be asserted. Eventually, VH will increase to a point that Vp and Vn are brought above Vp(min) and Vn(min), which will cause VH(en1) to deassert, which turns off the VH regulator 49 and allows VH to fall. As such, VH is controlled to an optimal level in a closed loop fashion by compliance voltage measurement and generation circuitry 51.

Operation of the compliance voltage measurement and generation circuitry 51 of FIG. 8B can thus prevent loading 99 of the pulses by increasing the compliance voltage VH, as illustrated in FIG. 8A. Note that after VH has been raised, Ve1 nor Ve2 stay bounded within region 111, which keeps the pulses from loading (99).

Various examples of the invention disclose passive tissue biasing circuitry which can mitigate the effect of voltage variation in the tissue, and therefore facilitate the sensing of neural responses, by passively holding the voltage of the tissue to a common mode voltage (Vcm). In examples of the invention, the IPG 100's conductive case electrode 12 is passively biased to Vcm using a capacitor, as opposed to actively driving the case electrode 12 to a prescribed voltage using a voltage source. Using the case electrode 12 to provide Vcm, while not strictly necessary, is sensible: a patient's tissue is of relatively low resistance, and the IPG's case electrode 12 is relatively large in area. Therefore, even if the case electrode 12 is implanted at a distance from the electrodes 16, the case electrode 12 still comprises a suitable means for establishing Vcm for the whole of the tissue. The passive tissue biasing circuitry however can also cause any electrode of the IPG 100, including the lead based electrodes 16, to set the common mode voltage of the tissue. Nonetheless, the bulk of this disclosure assumes use of the case electrode to set Vcm as a primary example.

As explained below, once Vcm is established at the case electrode 12 and hence in the tissue, voltages otherwise formed in the tissue, such as those accompanying the production of stimulation pulses, will be established relative to Vcm. This can ease sensing of small signals in the tissue, such as the sensing of neural responses (e.g., ECAPs). As explained below, Vcm may not be perfectly constant (i.e., it may be pseudo-constant), but nonetheless may be made to vary to a small enough degree to ease sensing.

The case 12 that houses the stimulation circuitry and other components is preferably entirely conductive, but, although not shown, may only be conductive at a portion. For example, the conductive case 12 may be insulative in parts, but conductive at a portion and able at such portion to produce the common mode voltage Vcm. In other words, the disclosed technique is effective even if the conductive case isn't entirely conductive but conductive only in part.

Figure 9A:
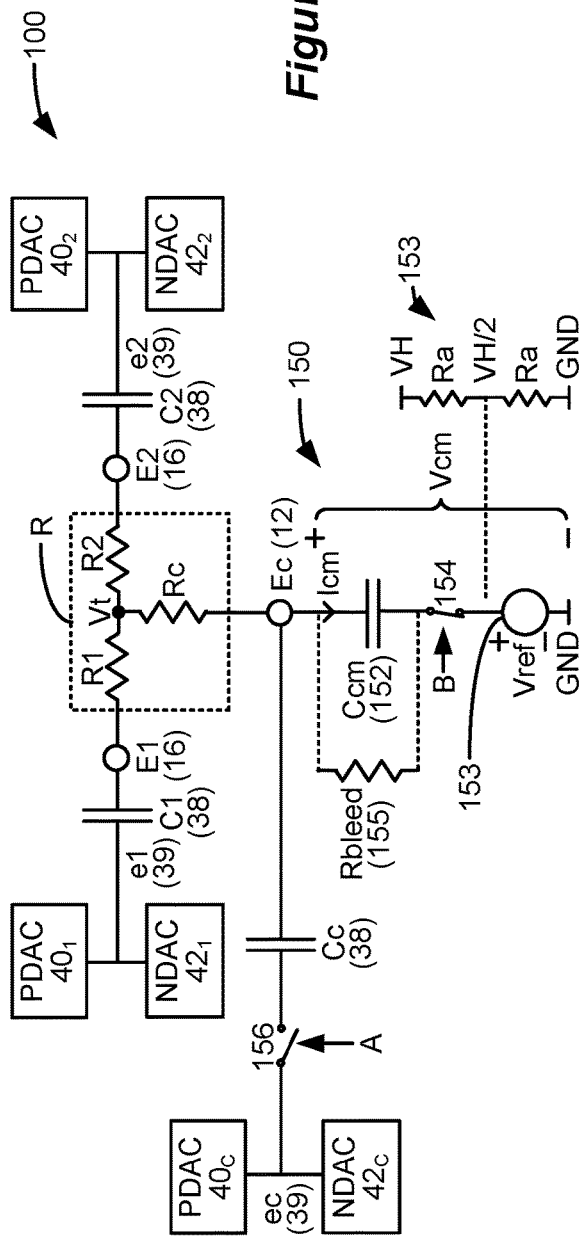
FIGS. 9A and 9B show first examples of passive tissue biasing circuitry configured to establish a common mode voltage in the tissue at the case electrode using a capacitor, as useful for example in the sensing of neural responses.

A first example of passive tissue biasing circuitry 150 configured to establish a common mode voltage Vcm in the tissue is shown in FIG. 9A. In this example, a capacitor Ccm 152 is provided between the case electrode Ec 12 at the capacitor's top plate and a reference voltage Vref at the capacitor's bottom plate, the magnitude of which is discussed below. A current Icm may flow through capacitor Ccm to assist in passively setting Vcm, as described further below. Ccm may also more generally comprise a capacitance, which may be comprised of a single capacitor or one or more capacitors or capacitances. A reasonable value for Ccm can depend on many factors, such as the maximum allowed ripple for Vcm, the degree of potential imbalance in the stimulation circuitry, and a maximum output current of an amplifier useable in the passive tissue biasing circuitry, all of which are discussed below. In any event, Ccm would typically range between 1 and 10 microFarads, and may comprise 4.7 microFarads in one example.

The reference voltage Vref may comprise a constant voltage provided by a voltage source 153 inside the conductive case Ec 12. Vref may be adjustable, and preferably has a value between or equal to ground (0V) and the compliance voltage (VH). Vref may also have a value that varies as a function of the compliance voltage VH, which as noted earlier may vary by operation of compliance voltage measurement and generation circuitry 51 (FIG. 8B). For example, Vref may be set to VH/2. In just one example, a voltage source 153 producing VH/2 may be formed as a voltage divider comprising a resistor ladder with serially-connected high resistances Ra, as shown to the right in FIG. 9A. The common mode voltage Vcm established in the tissue comprises the sum of any voltage across capacitor Ccm 152 and Vref. Note that voltage source 153 is not strictly necessary, particular if Vref equals zero, in which case the end of switch 154 (explained below) may simply be connected to ground.

Note that the tissue R between the case electrode Ec 12 and the electrodes selected for stimulation (E1 and E2) has been represented as a resistor network comprising resistances Rc, R1, and R2 coupled to electrodes Ec, E1, and E2. The relevance of this resistor network is described further below with reference to FIGS. 11A-11C.

Also shown in FIG. 9A are aspects of the stimulation circuitry 28 including the PDAC(s) $40_i$ and NDAC(s) $42_i$ connected to the various electrode nodes 39 ei. Such aspects of stimulation circuitry 28 are useful to show, particularly as concerns the case electrode, because as mentioned above the case electrode node ec/case electrode Ec 12 can be actively driven similarly to any other electrode 16 (e.g., during monopolar stimulation). However, such operation of the stimulation circuitry 28 to actively drive the case electrode is inconsistent with operation of passive tissue biasing circuitry 150, and so switches 156 and 154 are provided to isolate the two circuits 28 and 150.

When it is desired to actively drive the case electrode Ec 12 using stimulation circuitry 28 (e.g., $PDAC40_C$ or NDAC $42_C$), control signal A is asserted to close switch 156 to connect the stimulation circuitry 28 to the case electrode Ec 12, and control signal B is deasserted to open switch 154 to isolate capacitor Ccm 152 within the passive tissue biasing circuitry 150 from the case electrode 12. Alternatively, when using the passive tissue biasing circuitry 150 to passively set the common mode voltage Vcm in the tissue, control signal B is asserted to close switch 154 to connect capacitor Ccm 152 within the passive tissue biasing circuitry 150 to the case electrode 12, and control signal A is deasserted to open switch 156 to isolate the stimulation circuitry 28 from the case electrode 12. If the passive tissue biasing circuitry 150 need not operate, and if the case electrode is not being driven by stimulation circuitry 28, both of switches 154 and 156 can be open. Control signals A and B may be issued by the control circuitry 102 (FIG. 5) in the IPG 100, and switches 154 and 156 may also appear on the other side of their respective capacitors Ccm and Cc, or on the other side of voltage source 153. In FIG. 9A and subsequent figures, switch 154 is closed and switch 156 opened to focus discussion on operation of the passive tissue biasing circuitry 150.

Although not shown, activation of the passive tissue biasing circuitry 150 (and disconnection of the stimulation circuitry 28 from the case electrode Ec), can be affected by programming the IPG 100. For example, during periods when the IPG 100 is to sense neural responses and when neural response algorithm 124 (FIG. 5) is active, the control circuitry 102 can automatically close switch 154 and open switch 156. Such sensing need not always occur during operation of the IPG 100, and so the control circuitry 102 can open switch 154 at other times, thus allowing the case electrode Ec to be actively driven by the stimulation circuitry 28 if desired. External devices in communication with the IPG 100, such as the clinician programmer 70 or external controller 60 (FIG. 4), can also be used to place the IPG 100 in a neural sensing mode which will close switch 154 to allow the passive tissue biasing circuitry 150 to function to passively set a common mode voltage Vcm in the tissue. User interfaces of those devices 60 and 70 can have selectable options to affect this.

Figure 9B:
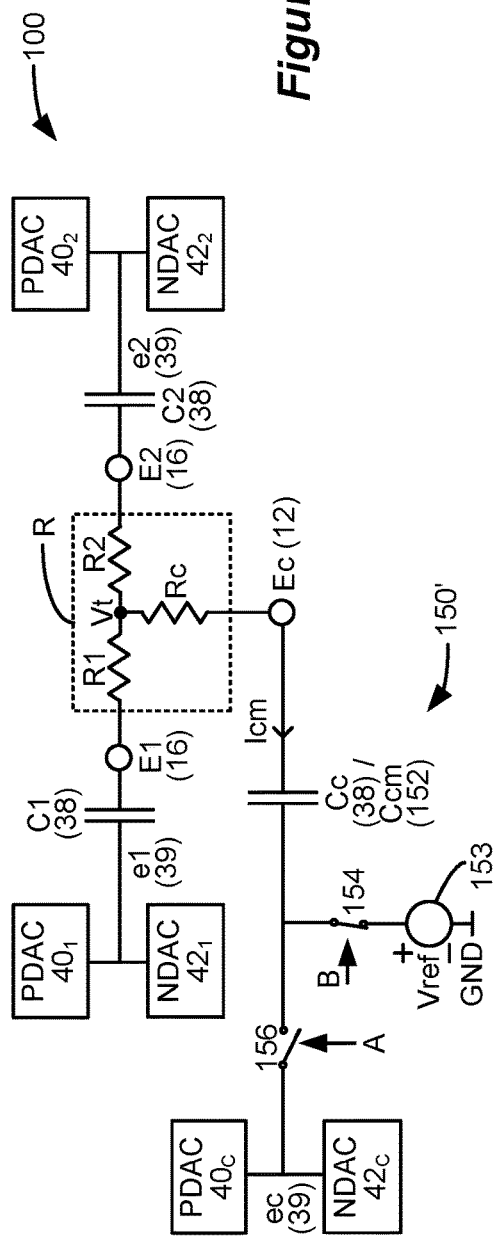

FIG. 9B shows a variation to the passive tissue biasing circuitry 150' in which the DC-blocking capacitor Cc 38 between electrode node ec and electrode Ec is also used as the capacitor Ccm 152 within the passive tissue biasing circuitry. Again, switches 154 and 156 and their respective control signals A and B allow either the passive tissue biasing circuitry 150' or the stimulation circuitry 28 to be connected to the case electrode Ec 12.

Figure 10A:
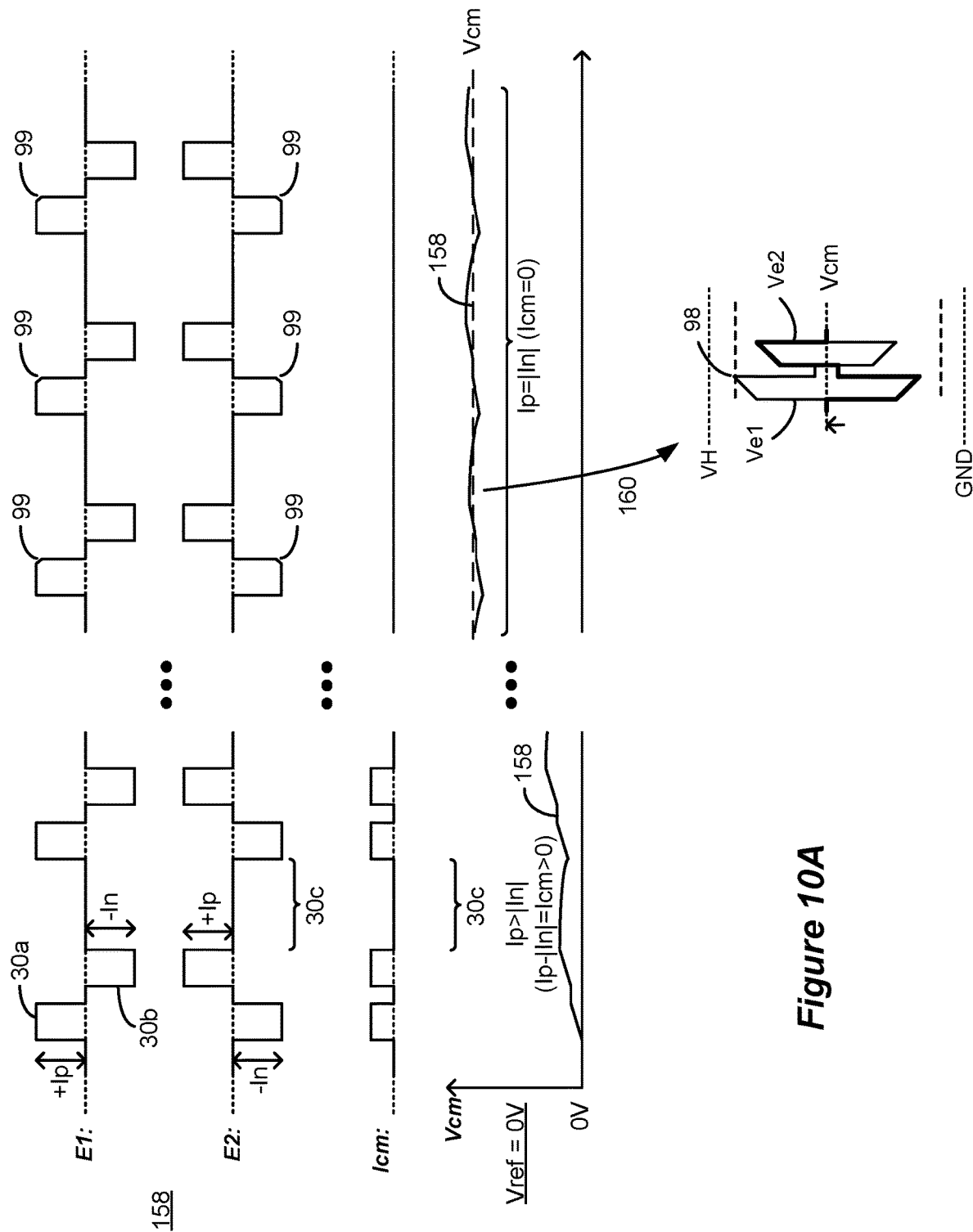
FIGS. 10A and 10B explain operation of the passive tissue biasing circuitry in establishing the common mode voltage in the tissue.
Figure 10B:
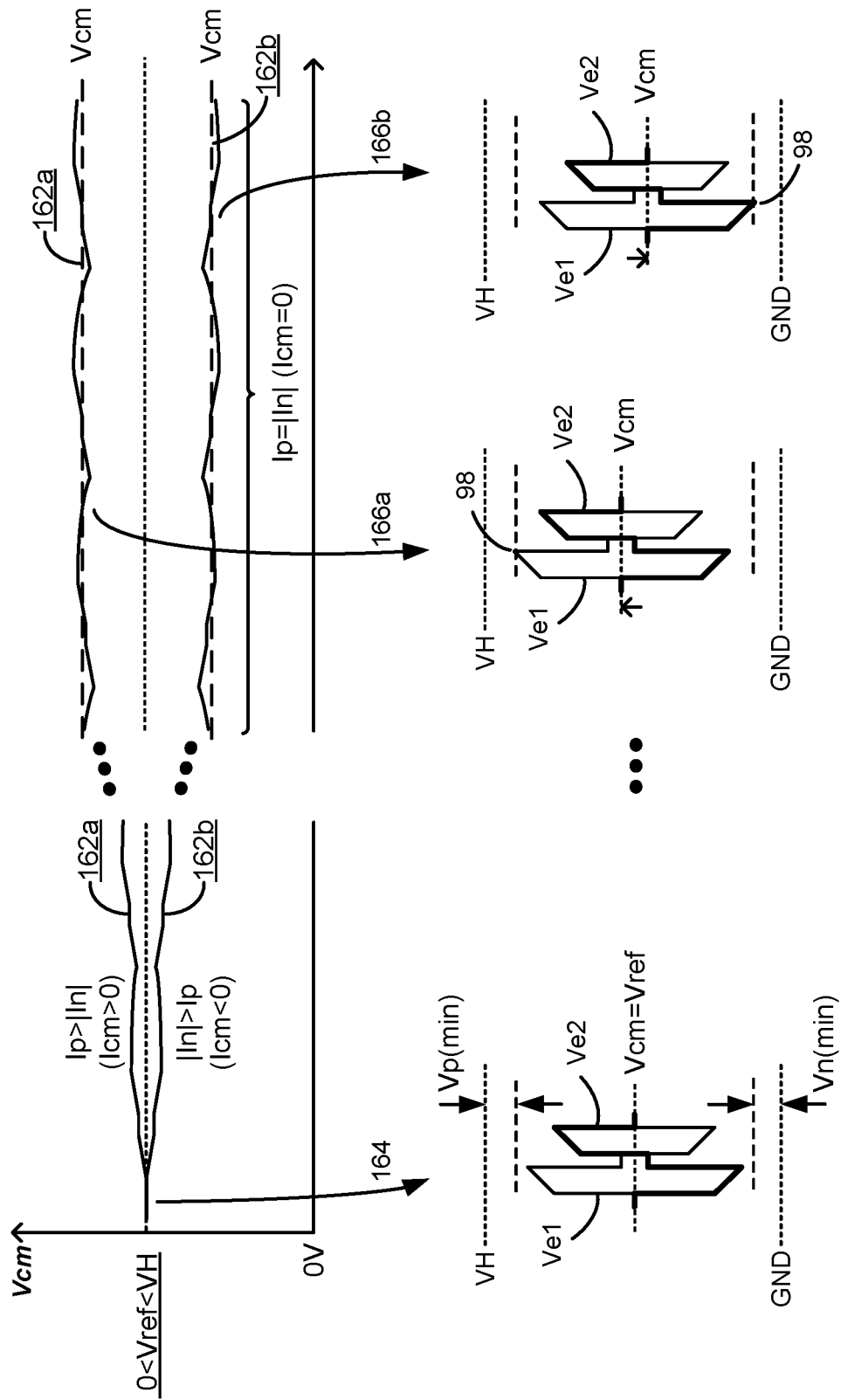

FIGS. 10A and 10B explain operation of the passive tissue biasing circuitry 150 or 150' (both simply referred to subsequently as 150), and show particularly how the circuitry operates if the PDAC(s) and NDAC(s) used to provide current pulses at the selected electrodes (again, E1 and E2 for illustration, but other electrodes can be chosen) have variation in the magnitudes of the currents Ip and In they provide (see FIG. 7A). As noted earlier, Ip and |In| are ideally equal in magnitude at any given time. But non-idealities may cause the amplitude of Ip and |In| to differ slightly, perhaps because of differences in PDAC and NDAC construction. Ip and |In| may also simply turn on and off at slightly different times if there is variation in the timing of the control of the PDACs and NDACs. Finally, Ip may not equal |In| if either of the PDACs or NDACs is not sufficiently powered, i.e., if the voltage drops Vp or Vn across them are not greater than or equal to Vp(min) or Vn(min) respectively. As explained earlier, Vp or Vn being too low can cause loading of the pulses (99, FIG. 8A), which may require enabling of the compliance voltage measurement and generation circuitry 51 to raise the compliance voltage (FIG. 8B).

The passive tissue biasing circuitry 150 is beneficial in its ability to handle such non-idealities and to set common mode voltage Vcm accordingly. In example 158 of FIG. 10A, it is assumed that Vref is set to zero Volts (e.g., voltage source 153 is not present). It is further assumed that Ip provided by the PDAC(s) is initially greater than the current provided by the NDAC(s) (i.e., Ip>|In|). In this case, the difference in these currents (Ip−|In|) comprises a positive current Icm that will initially flow through the capacitor Ccm 152 from the case electrode Ec 12 to ground during each pulse phase 30a and 30b. Any current Icm charges the capacitor Ccm 152, in this case with a positive voltage, which initially increases Vcm during each pulse phase 30a or 30b, as shown in FIG. 10A. (Vcm may decay slightly during quiet periods 30c between the pulses).

Establishing Vcm at the case electrode Ec, and hence in the tissue, causes electrode node voltages Ve1 and Ve2 to become referenced to this voltage. Thus, as Vcm rises, so too will Ve1 and Ve2 start to rise. Ve1 and Ve2 will eventually increase to a point at which Ve1 will just barely start in part 98 to exceed VH−Vp(min), as shown in waveform 160 of FIG. 10A. At this point, and as discussed earlier (FIG. 8A), the voltage drop Vp across the PDACs $40_1$ and $40_2$ becomes too small to support production of the slightly larger current Ip, causing minimal loading 99 of the first phase pulses 30a for electrode E1. (Such minimal loading 99 of the pulses would not significantly alter the stimulation therapy the pulses provide). Ip will thus eventually drop slightly to match the value of |In| (at least from a time-averaged or total charge standpoint), at which time Icm will equal 0. (Notice that Ip being loaded 99 also causes In to become loaded, since they are equal at this point). Icm=0 prevents capacitor Ccm from charging further, and thus Vcm is eventually established at a pseudo-constant level higher than Vref (ground), as shown in FIG. 10A.

If the NDAC(s) current In is higher than the PDAC(s)'s current Ip (i.e., |In|>Ip), Icm would flow as a negative current from ground to the case electrode Ec 12. This would establish Vcm as a negative voltage in example 158 (Vcm<Vref=0), which may be undesirable from a circuitry standpoint. To accommodate this possibility, in examples 162a and 162b of FIG. 10B, Vref is set by voltage source 153 to a value higher than zero but less than the compliance voltage VH (i.e., 0<Vref<VH). For example, Vref may be set to VH/2.

With Vref so set, Vcm will initially be set to Vref. Electrode node voltages Ve1 and Ve2 are thus initially referenced to Vcm=Vref, as shown in the waveform 164 of FIG. 10B.

If Ip>|In| as in example 162a, Icm will initially be positive causing a positive voltage to form across capacitor Ccm 152. The effect of passive tissue biasing circuitry 150 is then similar to what occurred in example 158 of FIG. 10A: Vcm will rise from Vref, and so too will Ve1 and Ve2, until Ve1 just barely (part 98) exceeds VH−Vp(min), as shown in waveform 166a. At this point, the voltage drop Vp across the PDACs $40_1$ and $40_2$ becomes too small to support production of the slightly larger current Ip during the first phase pulses 30a. Ip will thus drop slightly to match the value of |In|, with both becoming slightly loaded 99 (FIG. 10A), and thus Icm will equal 0. This prevents capacitor Ccm from charging further, establishing Vcm at a level higher than Vref. In effect, the example 158 of FIG. 10A and example 162a of FIG. 10B are similar, and would establish Vcm at the same value. It would simply take the example 158 longer to do so because it will take longer for Vcm to be established when Vref equals zero than when Vref is higher than zero.

If |In|>Ip as in example 162b, a negative current Icm will initially flow through the capacitor Ccm 152 from ground to the case electrode Ec 12. This charges the capacitor Ccm 152 with a negative voltage, which decreases Vcm from Vref during each pulse phase 30a or 30b. This causes Ve1 and Ve2 referenced to Vcm to also fall. Eventually, Ve2 will just barely (part 98) fall below Vn(min), as shown in waveform 166b of FIG. 10B. At this point, the voltage drop Vn across the NDACs $42_1$ and $42_2$ becomes too small to support production of the slightly larger current |In|. |In| will thus drop slightly to match the value of Ip, and thus Icm will equal 0. (Again, In being loaded 99 also causes Ip to become loaded, since they are equal at this point, as shown in FIG. 10A). Icm=0 prevents capacitor Ccm from charging further, establishing Vcm at a level lower than Vref, as shown in FIG. 10B. In short, in this example 162b, the fact that Icm is negative is not problematic from a circuitry standpoint because Vref is higher than zero, which allows Vcm to fall below Vref while still remaining positive.

Referring again to FIG. 9A, an optional bleed resistor Rbleed 155 is included in parallel with the capacitor Ccm 152. The bleed resistor Rbleed 155 is preferably of a high resistance (e.g., 1 MegaOhm or higher). Rbleed allows charge to bleed slowly off the capacitor Ccm, for example, during periods when the passive tissue biasing circuitry is not being used. Furthermore, Rbleed can assist with charge balancing, which can be helpful in preventing loading 99 of the current pulses. Rbleed permits a low current to flow, which current is proportional to the voltage across the capacitor Ccm. Assume for example that the PDAC(s) are slightly stronger than the NDAC(s), i.e., that Ip>|In| initially, causing Vcm to rise. As explained earlier, Vcm will continue to increase until the voltage across the stronger PDAC(s) starts to drop below Vp(min), causing Ip to drop to match |In|, thus achieving current balancing (and causing Icm to eventually equal 0). Beneficially, resistor Rbleed will start adding some current to the weaker NDAC(s), which may allow current balancing to happen before the PDAC(s) become loaded. Should this occur, there would be no loading (99) of the electrode current, and Vcm can reach equilibrium at a lower voltage. Essentially then, Rbleed acts as a current path to boost the weaker DAC. Note that Rbleed is not shown in subsequent examples of the tissue biasing circuitry for convenience, but could be used with any of these examples.

Figure 11A:
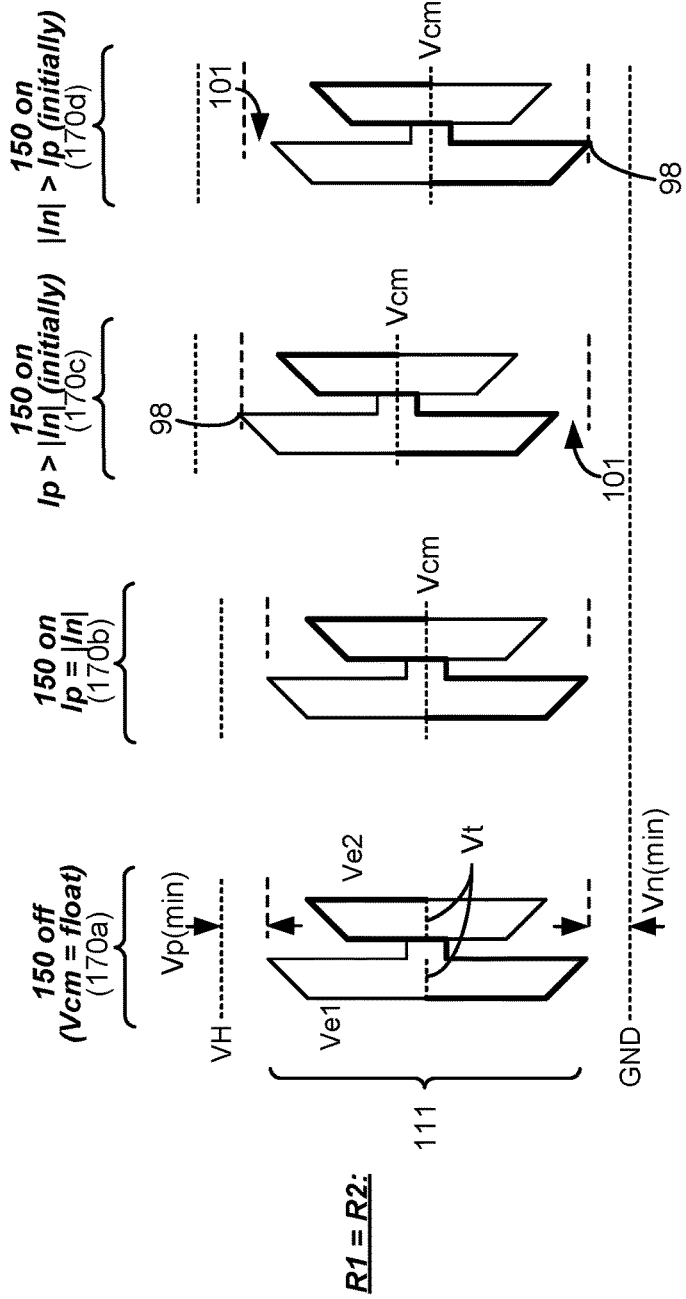
FIGS. 11A-11C explain operation of the passive tissue biasing circuitry given potential mismatches in electrode-to-case resistance and mismatches between the source and sunk current in the tissue.
Figure 11B:
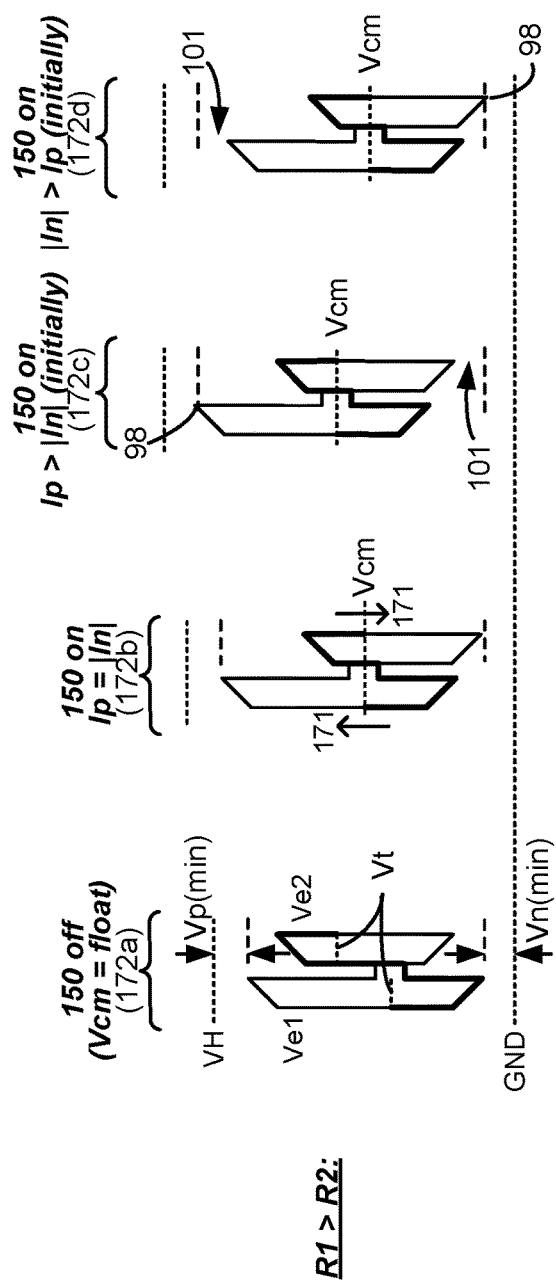
Figure 11C:
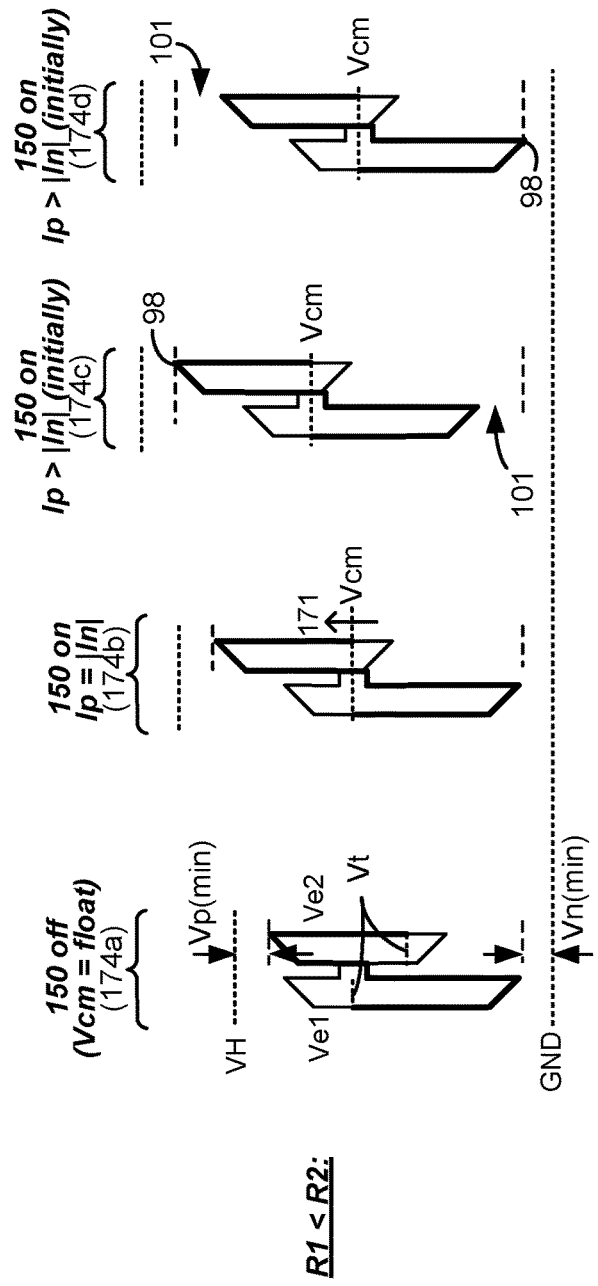

FIGS. 11A-11C further describe operation of the passive tissue biasing circuitry 150 under different circumstances. Further described is the relevance of the modelling the tissue R with resistances Rc, R1, and R2. Such modelling is useful to consider, because the resistance between each selected electrode E1 and E2 and the case electrode Ec may not be the same, which is not surprising given the complex tissue environment and distance between electrodes E1 and E2 and the case electrode Ec. In particular, R1 and R2 may vary. FIGS. 11A-11C further describe operation of the passive tissue biasing circuitry 150 if the magnitudes of Ip and In vary, and describe how compliance voltage measurement and generation circuitry 51 may operate to accommodate operation of the passive tissue biasing circuitry 150. In FIGS. 11A-11C, it is assumed that Vref has been set to VH/2.

In FIG. 11A, it is assumed that R1 equals R2 in the tissue model. Waveform 170a shows the electrode node voltages Ve1 and Ve2 when passive tissue biasing circuitry 150 is not used (e.g., switch 154 is opened, and Vcm at the case electrodes floats). Voltage Vt within the resistance model—indicative of the tissue voltage—floats to whatever level would otherwise be indicated by the stimulation. In this case, it is seen that Vt is the same during each of the pulse phases 30a and 30b. Assuming Vp(min) and Vn(min) are equal, Vt would be approximately VH/2. Further, assuming that compliance voltage measurement and generation circuitry 51 (FIG. 8B) is operating to adjust the compliance voltage to an optimal level, Ve1 and Ve2 would be generally be tightly pinned within region 111 between Vn(min) and VH−Vp(min).

For waveforms 170b-170d, passive tissue biasing circuitry 150 is used (e.g., switch 154 is closed), and thus a common mode voltage Vcm is passively established in the tissue as Ccm 152 is (possibly) charged. Ve1 and Ve2 become referenced to Vcm during each of pulse phases 30*a* and 30*b*.

In waveform 170*b*, Ip=|In|. Icm would equal zero, and Vcm is thus established at approximately VH/2 (Vref), just as occurred in waveform 170*a*.

In waveform 170*c*, it is assumed initially that Ip>|In|, as occurred in example 162*a* of FIG. 10B. Icm would initially be positive, which eventually drives Vcm, Ve1 and Ve2 higher for the reasons already explained. This would cause Ve1 to eventually surpass VH−Vp(min). Therefore, in this example, compliance voltage measurement and generation circuitry 51 (FIG. 8B) operates to raise VH to alleviate this problem. VH would gradually be raised until Ve1 just barely passes VH−Vp(min) as shown in waveform 170*c*, at which point compliance voltage measurement and generation circuitry 51 would stop increasing VH as shown in waveform 170*c*. Ip would equal |In| at this point, Icm would be zero, and Vcm would be established at a value higher than Vref. Note that increasing the compliance voltage VH also (further) increases Vcm in this example, because Vref (=VH/2) will also increase.

In waveform 170*d*, it is assumed initially that |In|>Ip, as occurred in example 162*b* of FIG. 10B. Icm would initially be negative, eventually driving Vcm, Ve1, and Ve2 lower. Note that this may eventually cause Ve2 to become lower than Vn(min). Again, measurement and generation circuitry 51 can operate to raise VH and alleviate this problem. Raising VH increases Vref (=VH/2), and hence Vcm, Ve1 and Ve2, until Ve2 is just barely below Vn(min) as shown in waveform 170*d*. |In| would equal Ip at this point and Icm would be zero. Even though the tendency would be for Vcm to decrease (Icm<0), raising VH also raises Vref, which counteracts to raise Vcm.

A comparison of waveforms 170*c* and 170*d* to waveform 170*b* in FIG. 11A shows that use of the passive tissue biasing circuitry 150 may warrant increasing the value of the compliance voltage VH if the currents Ip and In provided by the PDAC(s) and NDAC(s) are not balanced. Increasing the compliance voltage is generally not preferred as this draws extra power in the IPG 100, and will more quickly drain the IPG's battery 14 (FIG. 1). In particular, extra headroom 101 is provided within region 111, during which the voltage drops Vn across the NDACs (waveform 170*c*) and the voltage drops Vp across the PDACs (waveform 170*d*) are larger than those DAC require to produce the pulses with the prescribed amplitudes. However, this downside is offset by the benefit that a controlled common mode Vcm provides when sensing neural responses in the tissue.

In FIG. 11B, it is assumed that R1 is greater than R2 in the tissue model. Waveform 172*a* assumes that passive tissue biasing circuitry 150 is not used, and thus tissue voltage Vt floats to whatever level would otherwise be indicated by the stimulation. In this case, it is seen that Vt is different during pulse phases 30*a* and 30*b*: Vt is lower during pulse phase 30*a* because more voltage is dropped across R1 than R2; and Vt is higher during pulse phase 30*b* when the polarity of the current is reversed.

For waveforms 172*b*-172*d*, passive tissue biasing circuitry 150 is used (e.g., switch 154 is closed), and thus Vcm is passively established in the tissue as Ccm 152 is (possibly) charged. Ve1 and Ve2 are referenced to Vcm during each of pulse phases 30*a* and 30*b*, which in this example causes the waveforms to shift 171 during each of the pulse phases. Such shifting 171 tends to draw Ve1 and Ve2 upwards during the first pulse phase 30*a*, and downwards during the second pulse phase 30*b* as shown in waveform 172*b*.

In waveform 172*b*, it is assumed that Ip=|In|, which doesn't charge capacitor Ccm 152. Nonetheless, referencing Ve1 and Ve2 to Vcm may cause the compliance voltage to be too low given the shifting 171, and so in waveform 172*b* it is seen that the compliance voltage has been raised (51) so that Ve1 and Ve2 are still bounded by region 111 (FIG. 8A) to prevent the resulting pulses from becoming loaded (99).

A comparison of waveforms 172*a* and 172*b* shows that use of the passive tissue biasing circuitry 150 may warrant increasing the value of the compliance voltage, VH if the resistance between the active electrodes and the case electrode are not balanced. Again, while increasing VH is generally not desired for power consumption reasons, this downside is offset by the benefit that a common mode voltage Vcm provides when sensing neural responses in the tissue.

In waveform 172*c*, it is assumed initially that Ip>|In|, which eventually drives Vcm, Ve1, and Ve2 higher. This may cause Ve1 to surpass VH−Vp(min). The compliance voltage VH can therefore be raised even higher (51) to prevent pulse loading as shown. Again, increasing compliance voltage VH also increases Vref, which increases Vcm even further in this example.

In waveform 172*d*, it is assumed |In|>Ip, which drives Vcm, and Ve1 and Ve2, lower. This may cause Ve1 to become lower than Vn(min) during the second pulse phase 30*b*. The compliance voltage VH can therefore be raised even higher (51) to prevent pulse loading, as occurred with waveform 170*d* (FIG. 11A).

Notice again by comparing waveforms 172*c* and 172*d* to waveform 172*b* that use of the passive tissue biasing circuitry 150 may warrant even further increasing the value of the compliance voltage VH if the currents Ip and In provided by the PDAC(s) and NDAC(s) are not balanced, as described previously with respect to waveforms 170*b*-170*d* (FIG. 11A). Again, this downside is acceptable given the benefit that a common mode Vcm provides in the tissue.

In FIG. 11C, it is assumed that R1 is less than R2 in the tissue model. Waveforms 174*a*-174*d* show conditions analogous to waveforms 172*a*-172*d* of FIG. 10B, which again shows how operation of the passive tissue biasing circuitry 150 causes Ve1 and Ve2 to be referenced to Vcm as beneficial to neural sensing, but which may also warrant increasing compliance voltage VH (51) to prevent pulse loading.

Passive tissue biasing circuitry 150 is thus useful in passively setting Vcm in the tissue to an appropriate value despite any imbalance between Ip and In provided by the PDAC and NDAC circuitry and despite any imbalance in resistance R1 and R2 between the active electrodes and the case electrode Ec. As has been shown, the common mode voltage Vcm established at the case electrode Ec by passive tissue biasing circuitry 150 will passively change from Vref provided by voltage source 153 when there is an imbalance, thus eventually causing the current to the case (Icm) to equal zero. This is beneficial when compared to actively driving the case electrode to a set voltage. Actively driving a particular voltage at the case electrode cannot guarantee that current will not flow through the tissue to the case electrode. Such case electrode currents can lead to unwanted "pocket stimulation," meaning that current flows from the selected electrodes to the tissue pocket where the case 12 is implanted. Pocket stimulation may be felt by the patient, or may otherwise negatively affect therapy provided by the selected lead electrodes.

Figure 12A:
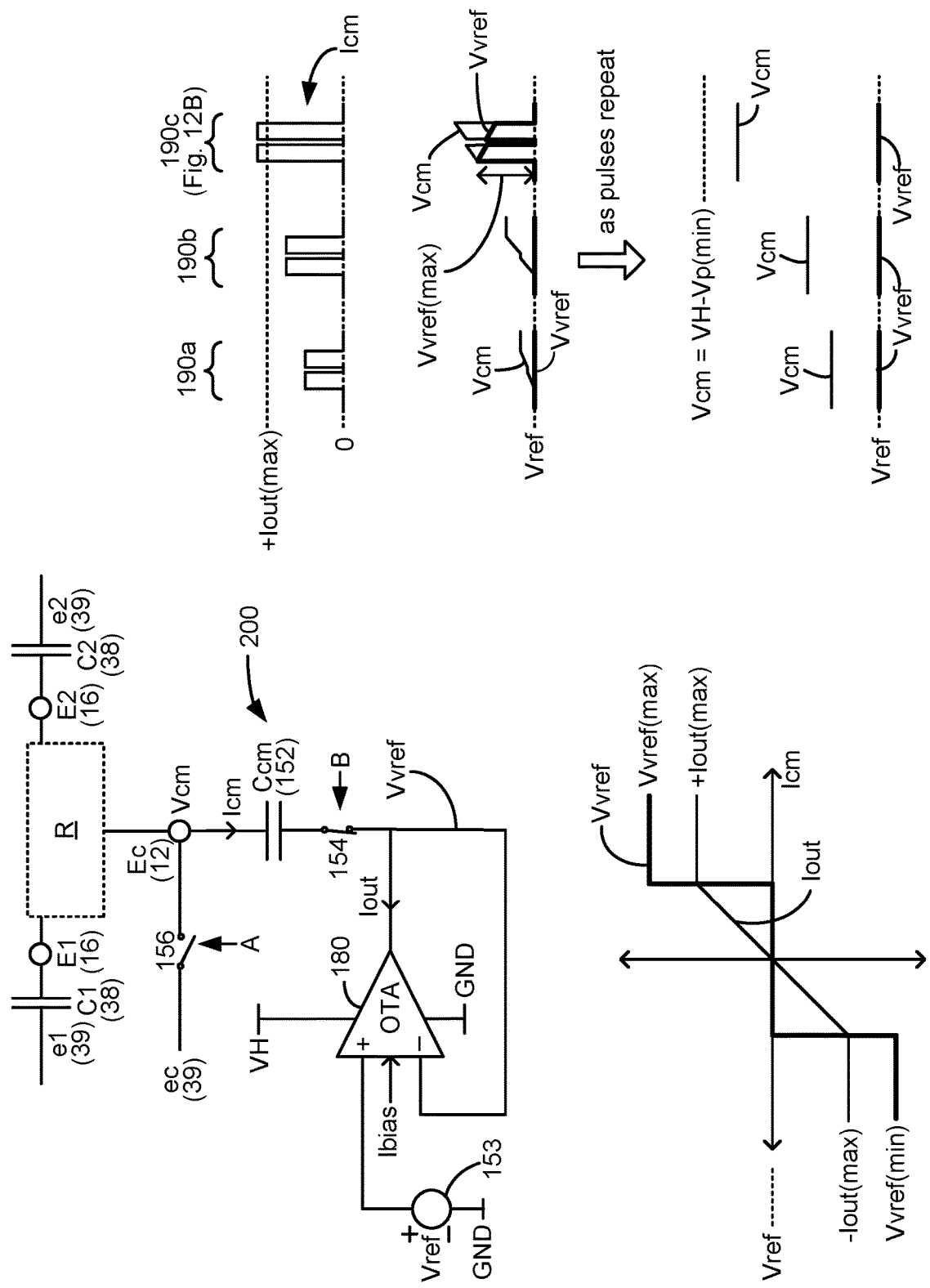
FIGS. 12A and 12B show a second example of passive tissue biasing circuitry including an amplifier for producing a virtual reference voltage for the capacitor and for limiting the current through the tissue to the case.

FIG. 12A shows another example of passive tissue biasing circuitry 200 that can be used to hold tissue at a common mode voltage Vcm. Passive tissue biasing circuitry 200 essentially works similarly to passive tissue biasing circuitry 150, but includes an amplifier 180, preferably an operational transconductance amplifier (OTA), which establishes a virtual reference voltage, Vvref, at the bottom plate of capacitor Ccm 152. Note that passive tissue biasing circuitry 200 may as before include switches 154 and 156 to selectively isolate the stimulation circuitry 28 and the passive tissue biasing circuitry 200, as explained earlier with reference to FIG. 9A. As also explained with reference to FIG. 9B, the capacitor used in passive tissue biasing circuitry 200 can comprise the case electrode's DC-blocking capacitor Cc 38, although this variation is not shown in FIG. 12A.

The OTA 180 establishes an output current, Iout that scales with a difference in the voltages at its inputs: i.e., Iout=(Vref−Vvref)*G, where G comprises the transconductance of the OTA 180. The OTA 180's has a positive and negative maximum output current +Iout(max) and −Iout (max). The absolute value of these maximum output currents, |Iout(max)|, is a function of a bias current, Ibias, provided to the OTA 180: |Iout(max)|=Ibias*A, where A comprises the current gain of the amplifier. In one example, current gain A=1000 and Ibias=100 nanoAmps, which allows Iout to range from −Iout(max)=−100 microAmps to +Iout(max)=100 microAmps. Either through design of the OTA 180 or adjustment of Ibias, −Iout(max) and +Iout(max) can be adjusted to different values.

OTA 180 is preferably configured as a follower, in which the virtual reference voltage Vvref is fed back to the negative input of the OTA. The positive input of the OTA 180 is provided with reference voltage Vref. Vref as before may be provided by a voltage source 153, and as before may comprise a constant or adjustable voltage preferably between or equal to ground (0V) and the compliance voltage (VH), such as VH/2. When connected as a follower, the OTA 180's output Vvref will equal Vref so long as Icm is between −Iout(max) and +Iout(max), as explained further below.

Operation of passive tissue biasing circuitry 200 can be understood with the assistance of the graphs in FIG. 12A. Given the polarity with which Iout is defined in FIG. 12A, Iout=Icm when Icm is between −Iout(max) and +Iout(max). When in this range, Icm simply passes as Iout through the OTA 180. Because the output current of the OTA 180 is not exceeded in this range, virtual reference voltage Vvref remains constant and equal to Vref.

Examples 190a and 190b show operation when Icm is positive and below +Iout(max). Example 190a shows a small mismatch between Ip and |In|, and thus a relatively small current Icm. At this current level, Vcm initially increases as capacitor Ccm is charged, while Vvref stays equal to Vref. Eventually (as the pulses repeat), Vcm stabilizes at a constant level, as explained earlier (FIGS. 10A-10B). Example 190b shows a higher mismatch between Ip and |In|, and thus a higher current Icm. This will charge the capacitor Ccm faster, and Vcm will rise faster and will eventually be established at a higher value. Although not shown, it should be understood that negative values for Icm would establish Vcm at level below Vref.

If the mismatch between Ip and |In| is large, such that Icm would exceed +Iout(max) as in example 190c, the OTA 180 will only be able to draw +Iout(max), thus capping Icm to this value. Having the OTA 180 limit Icm provides a benefit to passive tissue biasing circuitry 200 of FIG. 12A, because limiting Icm limits "pocket stimulation," which as explained earlier can be caused when unwanted current flows to the tissue pocket where the case 12 is implanted. In this regard, the OTA 180 can be designed to set +Iout(max) and −Iout (max) to appropriate values to limit the potential magnitude of pocket stimulation.

Returning to example 190c, because the OTA 180 cannot accommodate all of the excess current, Vcm and Vvref will initially be pulled above Vref to a value Vvref(max), which will vary in magnitude as further pulses are issued. (Again, Vref can be set to VH/2 to allow for pulling Vvref downward if Icm is negative, with the OTA 180 limiting Icm to −Iout(max)). Capacitor Ccm will then start to charge in a current-limited fashion (with Icm=+Iout(max)), causing Vcm to increase and Vvref to decrease. As the capacitor Ccm continues to charge upon the issuance of subsequent pulses, and as shown further in FIG. 12B, Vcm will continue to rise, and Vvref will continue to fall. As noted earlier, Vcm rising will cause the electrode node voltages (e.g., Ve1 and Ve2 to rise), eventually to a point at which one of the waveforms will start to breach VH−Vp(min), which causes dominant current Ip to fall to match |In|, as explained earlier (FIGS. 10A-10B). At this point Icm will equal zero, halting further charging of the capacitor, Ccm, and establishing Vcm at a value below VH−Vp(min). Note also that Vvref will return to Vref when Icm equals zero. Again, negative values for Icm would establish Vcm at level below Vref, but above Vn(min).

Figure 13A:
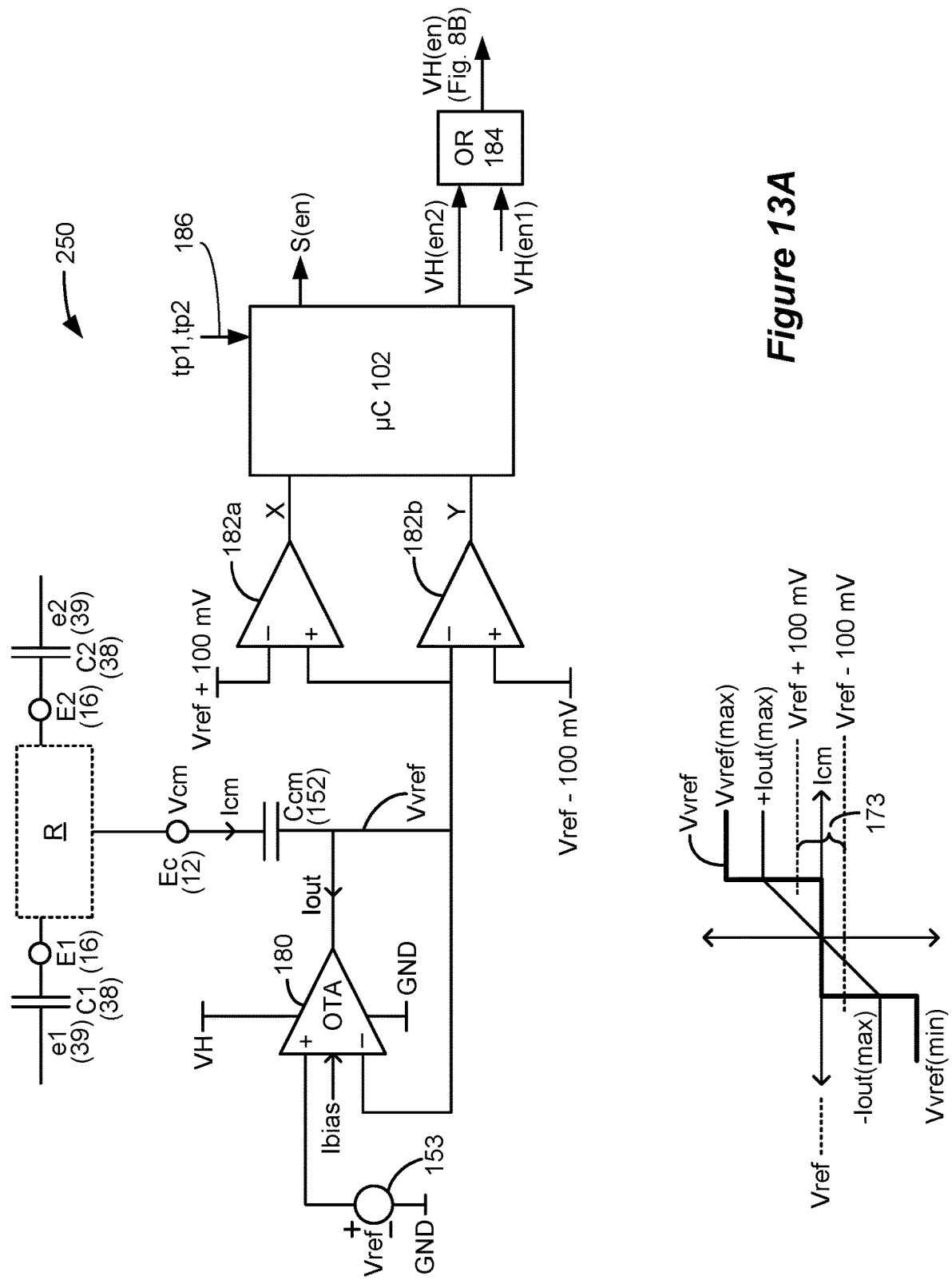
FIGS. 13A and 13B show a third example of passive tissue biasing circuitry including circuitry to sense the virtual reference voltage as helpful to enabling sensing of neural responses, and as helpful to adjusting the compliance voltage for the current generation circuitry.

FIG. 13A shows another example of passive tissue biasing circuitry 250 (switches 154 and 156 not shown) which adds optional additional circuitry for monitoring the virtual reference voltage, Vvref. Switches 154 and 156 are not shown for simplicity.

A window comparator as logic circuitry is provided comprising two comparators 182a and 182b. Each comparator 182a and 182b receives Vvref and a reference voltage that sets a window 173 around Vref. In the example shown, window 173 is 200 mV wide, and is set from Vref−100 mV to Vref+100 mV. Vref+100 mV is provided to comparator 182a, while Vref −100 mV is provided to comparator 182b. Voltages Vref−100 mV and Vref+100 mV may be provided by voltage sources similar to source 153 that produces Vref, although such additional sources are not shown. By connecting Vvref, Vref+100 mV, and Vref−100 mV to the appropriate positive and negative inputs of the comparators, comparator 182a's output X will equal a '1' if Vvref>Vref+100 mV, and comparator 182b's output Y will equal a '1' if Vvref<Vref−100 mV. Outputs X and Y will equal '0' if Vvref is between Vref+100 mV and Vref−100 mV. A plus-minus value of 100 mV for window 173 is just one example, and a different value could be used. An output providing at least one indication that Vvref has exceeded the Vref+100 mV or has fallen below the Vref−100 mV could also be used.

Outputs X and Y are provided to control circuitry 102, allowing virtual reference voltage Vvref to be monitored at appropriate times as discussed further below. Such monitoring is useful in a couple of different respects. First, it allows the control circuitry 102 to decide when neural response sensing is best performed in the IPG 100, which can be effectuated by having control circuitry issue sensing enable signal S(en), as explained further with reference to FIGS. 14A and 14B.

Second, monitoring Vvref is also useful to allow the control circuitry 102 to decide whether the compliance voltage VH should be raised. Raising the compliance voltage VH can be effected by asserting enable signal VH(en2), which can be sent to the input VH(en) of the PWM 53 of the compliance voltage measurement and generation circuitry 51 (FIG. 8B) which as explained earlier will activate VH regulator 49 to raise the compliance voltage. In this regard, the VH regulator 49 may be activated at its input either by enable signal VH(en1) provided by the measurement circuitry in the compliance voltage measurement and generation circuitry 51 as already explained, or by the assertion of VH(en2). This alternative is particularly useful because VH(en1) can operate when the passive tissue biasing circuitry 250 is not operating (switch 154 is open), while VH(en2) can operate when the passive tissue biasing circuitry 250 is operating (switch 154 is closed). OR gate 184 in FIG. 13A can be used to process the two enable signals VH(en1) and VH(en2) and assert input VH(en) when either is active. In another example, the VH regulator 49 may be activated exclusively by enable signal VH(en2), mooting the need for measurement circuitry in the compliance voltage measurement and generation circuitry 51.

Figure 13B:
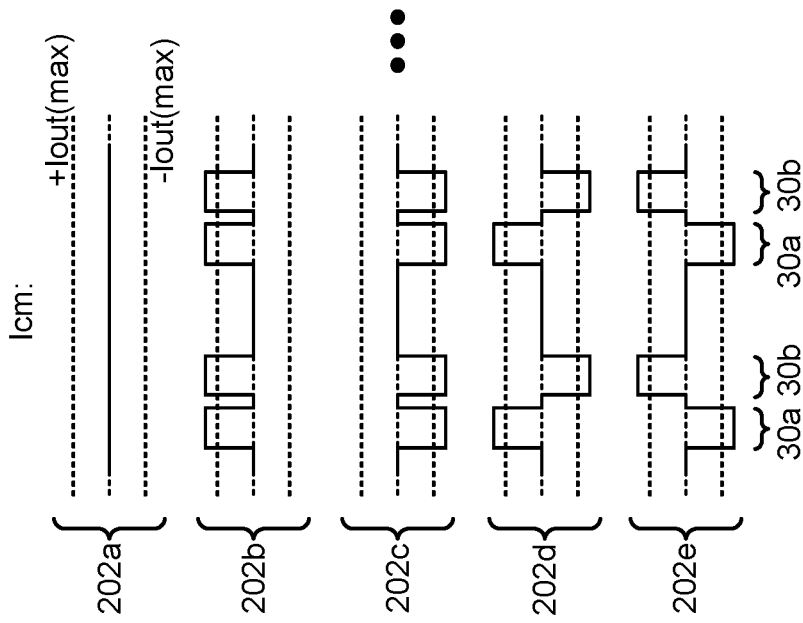

FIG. 13B explains the operation of passive tissue biasing circuitry 250 and how control circuitry 102 can be used to issue control signals S(en) to enable neural sensing and VH(en2) to increase the compliance voltage. It is useful that the control circuitry 102 review the status of outputs X and Y from the window comparator during both first 30a and second 30b phases of the biphasic pulses, as either pulse phase may provide information relevant to neural sensing or compliance voltage adjustment. Note that control circuitry 102 may know when the first and second pulses phases 30a and 30b are occurring, and thus when outputs X and Y should be sampled, because it may program the stimulation circuitry 28 with this timing information. Otherwise, the control circuitry 102 can receive one or more control signals 186 (tp1, tp2) from the stimulation circuitry 28 indicative of when stimulation is occurring during the first and second pulse phases 30a and 30b. Control signals tp1 and tp2 may be asserted to inform the control circuitry 102 when it is to sample outputs X and Y, which may be programmed to occur nearer to the ends of the pulse phases 30a and 30b when charging of the DC-blocking capacitors 38 is most severe, and hence when the electrode node voltages (e.g., Ve1 and Ve2) are most likely to breach region 111 (see, e.g., FIG. 7B).

Example 202a in FIG. 13B occurs when Icm passing through the capacitor Ccm is within the OTA 180's output current limits during both pulse phases, i.e., when −Iout(max)<Icm<+Iout(max). During this example 202a, Vvref would be within window 173, and generally equal to Vref, and outputs X and Y would equal '0' during both pulse phases. Vcm would be steady, and hence control circuitry 102 can enable sensing at this time by asserting S(en). Moreover, there is no reason to believe that compliance voltage VH is insufficient at this point so as to warrant enabling the VH regulator 49 per VH(en2).

Figure 12B:
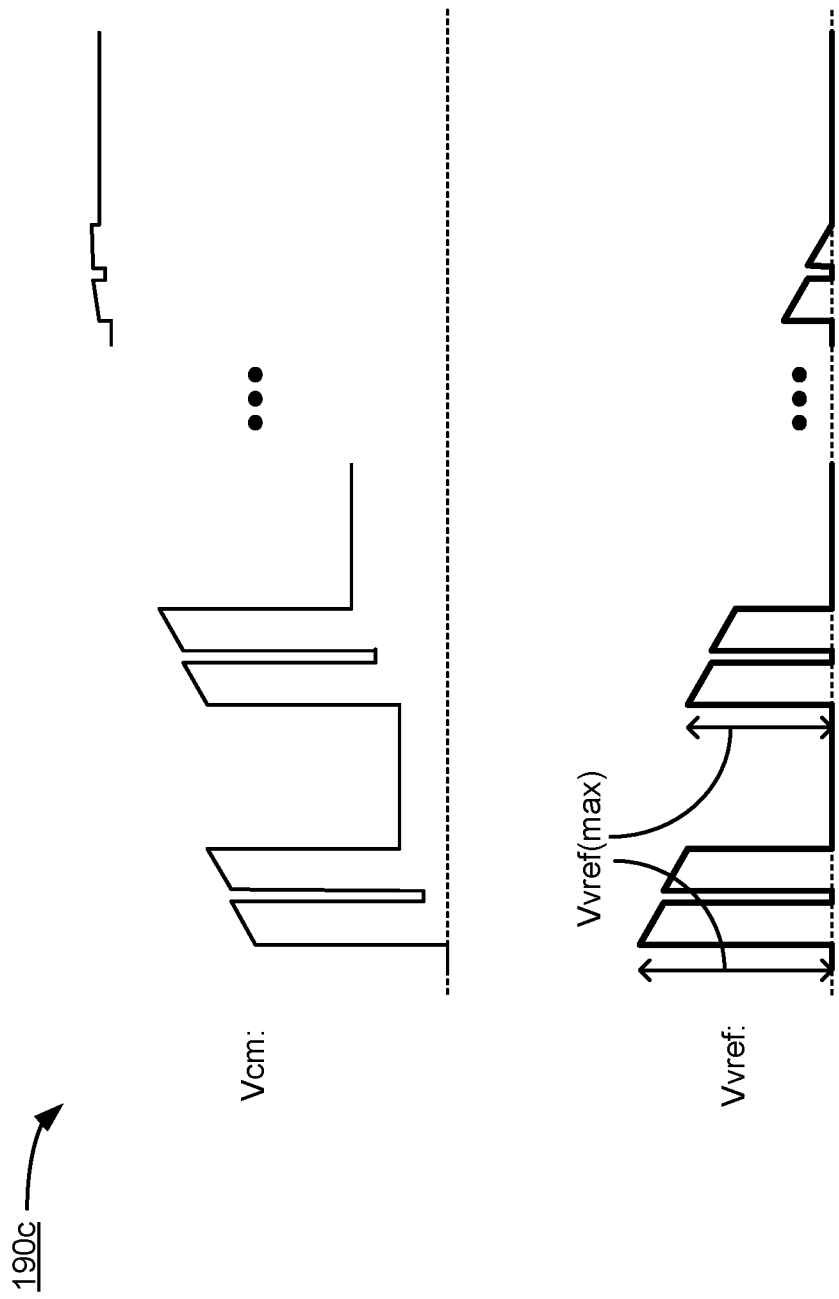

During example 202b, a significant positive current Icm>+Iout(max) occurs during both pulse phases 30a and 30b. During this example 202b, Vvref would be outside of window 173, i.e., Vvref>Vref+100 mV. Output X would therefore equal '1' during both pulse phases, while output Y would equal '0.' Vcm would not be steady, as shown in FIG. 12B. Hence, control circuitry 102 would disable sensing at this time by deasserting S(en). There is no still reason to believe that compliance voltage VH is insufficient at this point. Instead, the capacitor Ccm may merely be charging to a steady state, as occurred in FIG. 12B. Therefore, the control circuitry 102 would thus deassert VH(en2).

Example 202c is essentially the opposite of example 202b, having a significant negative current Icm<−Iout(max) during both pulse phases 30a and 30b. During this example 202c, Vvref would be outside of window 173, i.e., Vvref<Vref+100 mV. Output X would therefore equal '0' during both pulse phases, while output Y would equal '1.' Vcm would not be steady, because it would be in the process of decreasing below Vref. Hence, control circuitry 102 would disable sensing at this time by deasserting S(en). There is again no reason to believe that compliance voltage VH is insufficient at this point, because the capacitor Ccm may still be charging to a steady state. Therefore, the control circuitry 102 would thus deassert VH(en2).

During example 202d, it is seen that Icm is significantly positive (>+Iout(max)) during the first pulse phase 30a and significantly negative (<−Iout(max)) during the second pulse phase. During the first pulse phase 30a, Vvref would be higher than Vref+100 mV, and output X would equal '1', while output Y would equal '0'. During the second pulse phase 30b, Vvref would be lower than Vref−100 mV, and these logic states are flipped, with output X equaling '0' and output Y equaling '1.' Vcm would not be steady, and thus control circuitry 102 would disable sensing at this time by deasserting S(en). Moreover, this example 202d would not suggest that capacitor Ccm is merely on its way to being charged to a steady state, as the current Icm flowing through the capacitor is reversed during the two pulse phases. Instead, this example would suggest that the compliance voltage is insufficient: the NDACs are apparently loaded (Vn<Vn(min)) during the first pulse phase 30a (when Ip predominates), and the PDACs are apparently loaded (Vp<Vp(min)) during the second pulse phase 30a (when In predominates). This suggests that the electrode node voltages (e.g., Ve1 and Ve2) cannot stay within region 111 (FIG. 8A). Therefore, the control circuitry would assert VH(en2) during this example 202d.

Example 202e is essentially the opposite of example 202d, with the predominance in Icm flipped during the two pulse phases. Again, the control circuitry 102 would deassert S(en) and assert VH(en2).

Figure 14A:
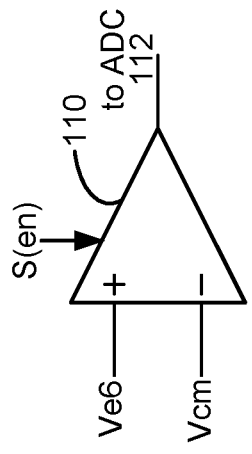
FIGS. 14A and 14B show sensing of a neural response at both a single electrode and differentially at two electrodes once the common mode voltage is established.
Figure 14A:
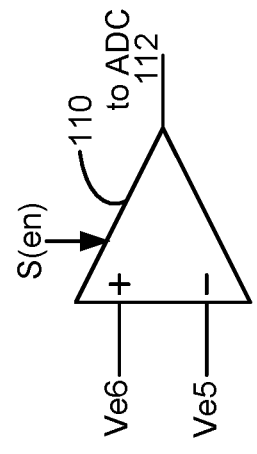
Figure 14A:
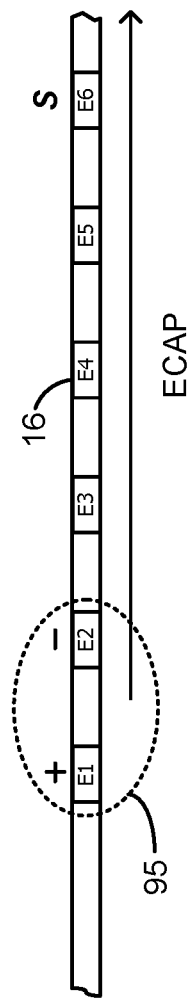
Figure 14B:
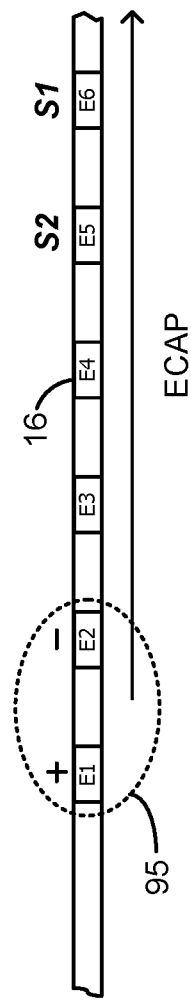

FIGS. 14A and 14B show how the generation of the common mode voltage Vcm can be used to assist in sensing neural responses in the tissue. In both of these figures, the sense amp 110 used to sense the neural response can be enabled to sense only when an enable signal, S(en), is asserted. This enable signal can be generated by the control circuitry 102 as explained with reference to FIGS. 13A and 13B, or could be generated in other manners and at other times.

FIG. 14A shows single ended sensing (S) of a neural response at a selected electrode E6 as explained earlier. Electrode node voltage Ve6 is provided to one input of the sense amp 110, while the other input receives Vcm as generated at the case electrode. Ve6 would also be referenced to Vcm present in the tissue. Because Vcm is stable in the tissue, the sense amp 110 is better able to reject this voltage, and sense the small signal neural response.

FIG. 14B shows differential sensing (S1 and S2) at different electrodes E5 and E6. Electrode node voltages Ve5 and Ve6 are provided to the input of the sense amp 110, both of which are referenced to Vcm. Again, this assists in sensing the small signal neural response.

The disclosed examples of passive tissue biasing circuitry are particularly useful in sensing neural responses, but could be useful in other context as well where it is beneficial that the common mode voltage in the tissue be set or well controlled. Further, while the passive tissue biasing circuitry has been shown as operating while any two electrodes are selected (e.g., E1 and E2), the circuitry can also operate if any two or more electrodes are selected for stimulation (e.g., electrodes E1 and E2 as anodes outputting a summed anodic current +I, and electrode E3 as a cathode outputting cathodic current −I).

Figure 15:
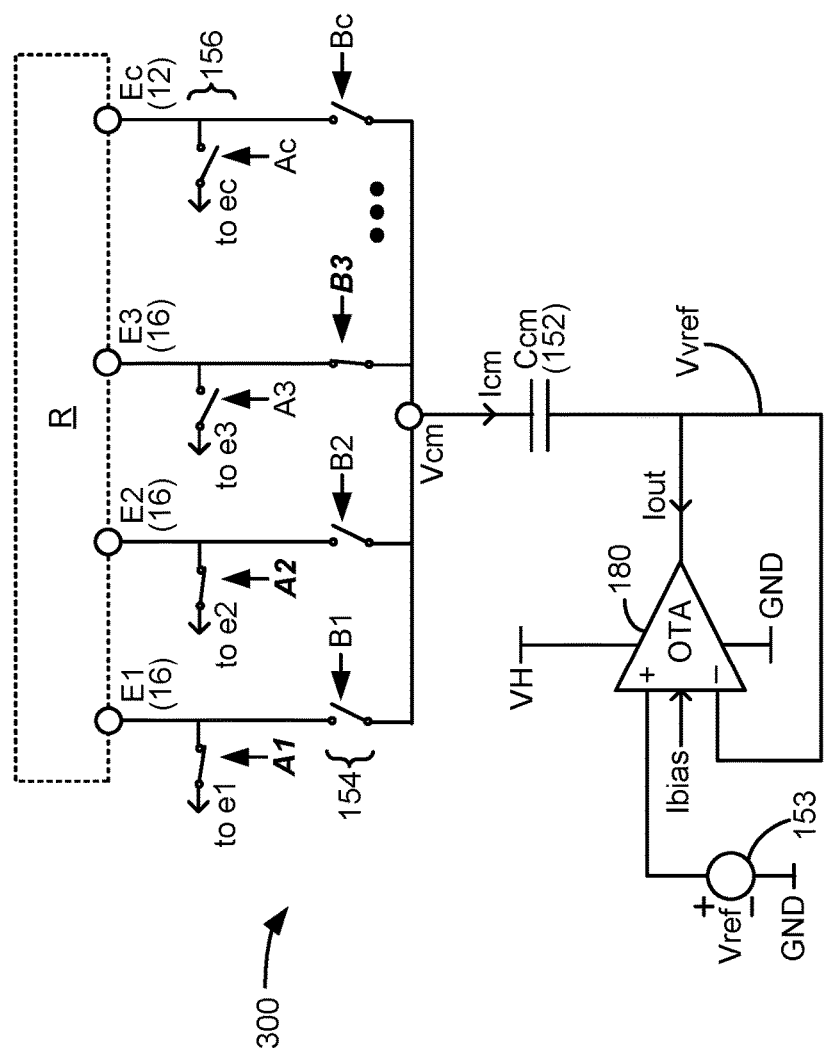
FIG. 15 shows an alternative in which the passive tissue biasing circuitry can allow any electrode (beyond the case electrode) to comprise the electrode used to set the common mode voltage in the tissue.
Figure 15:
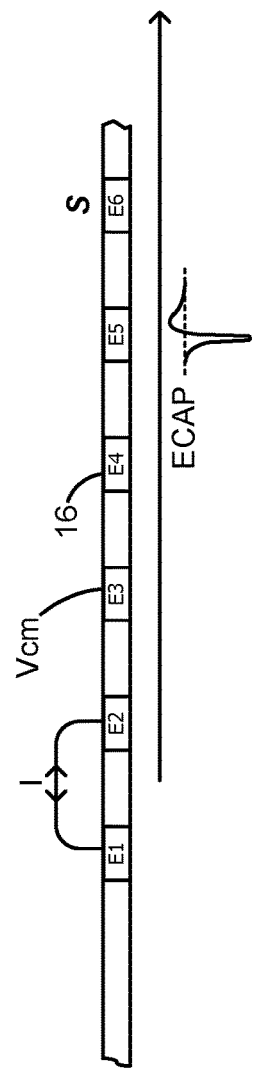

To this point in the disclosure it has been assumed that the case electrode Ec 12 comprises the electrode that is used by the passive tissue biasing circuitry to set the common mode voltage Vcm in the tissue. However, any electrode, including the lead-based electrodes 16 (FIG. 1), could also be used for this purpose. FIG. 15 shows this alternative to passive tissue biasing circuitry 300, and comprises an example in which any electrode, such as any lead-based electrode 16 or the case electrode Ec 12, can be chosen to set the common mode voltage, Vcm. The example shown in FIG. 15 corresponds generally to circuitry 200 (FIG. 12A), although any of 150 (FIG. 9A), 150' (FIG. 9B), or 250 (FIG. 13A) could employ the alternative circuitry of FIG. 15.

In FIG. 15, switches 154 and 156 have each been expanded to comprise a matrix of switches, with one switch 154 and one switch 156 associated with each of the lead-based electrodes (E1, E2, etc.) and the case electrode Ec. Switches 154 and switches 156 are similar in functionality to the individual switches 154 and 156 described earlier. Switches 156 are used to couple each electrode Ei to the stimulation circuitry 28 (not shown) via electrode nodes ei, while switches 154 are used to couple each electrode Ei to the common mode capacitor Ccm. Thus, in this example, the common mode capacitor Ccm is shared by the electrodes; in another example, each electrode could include its own dedicated capacitor for setting Vcm.

In the example shown at the bottom of FIG. 15, it is assumed that electrodes E1 and E2 have been selected as active to provide biphasic stimulation (I) to the tissue, while electrode E3 will provide the common mode voltage, Vcm. Switches 156 coupled to active electrodes E1 and E2 are thus closed (control signals A1 and A2 are asserted) to connect these electrodes to the stimulation circuitry 28. Because it is inconsistent to also provide Vcm at these active electrode nodes, their switches 154 are opened (control signals B1 and B2 are deasserted) to disconnect these electrodes from the capacitor Ccm. By contrast, electrode E3 which will establish the common mode voltage Vcm for the tissue will have its switch 154 closed (control signal B3 is asserted) to connect E3 to the capacitor Ccm. Because it is inconsistent to also drive electrode E3 with the stimulation circuitry 28, its switch 156 is opened (control signals A3 is deasserted). All other switches not associated with electrodes E1, E2, or E3 can be opened, as they are not in this example involved in either driving a tissue current or providing a common mode voltage Vcm.

Note that more than one electrode can be selected to provide the common mode voltage. For example, electrodes E3 and E4 can be selected to both provide Vcm (asserting B3 and B4), or electrodes E3, E4, and the case electrode Ec can all be selected to provide Vcm (asserting B3, B4, and Bc). Electrode(s) selected to sense the neural response—such as electrode E6 in the example of FIG. 15—would not be selected to participate in providing Vcm to the tissue. That is, E6's switch 154 would be open (B6 deasserted) as would its switch 156 (A6 deasserted) because E6 would not be driven by the stimulation circuitry 28 while sensing.

Providing Vcm to an electrode closer to those being used for stimulation may assist in referencing the electrode node voltages to Vcm. Furthermore, allowing a non-case electrode 16 to provide Vcm allows the case electrode Ec 12 to be actively driven (Ac asserted; Bc deasserted), such as during monopolar stimulation, while still providing the benefits that Vcm generation provides.

Although not illustrated, the IPG 100 could include one or more special electrodes anywhere on the device for setting Vcm, which electrode(s) may be dedicated to Vcm generation and not useable to provide stimulation to the tissue, R.

Although particular embodiments of the present invention have been shown and described, the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A stimulator device system, comprising:
a plurality of electrode nodes, each electrode node configured to be coupled to one of a plurality of electrodes configured to contact a patient's tissue;
stimulation circuitry configured to provide a stimulation current through the patient's tissue via at least one of the plurality of electrode nodes, wherein the stimulation circuitry is configured to be powered between a compliance voltage and a ground, wherein the compliance voltage varies as a function of time; and
biasing circuitry configured to provide a common mode voltage at one or more first of the electrodes, wherein the common mode voltage is derived from the compliance voltage and varies as a function of time.

2. The system of claim 1, wherein the biasing circuitry is configured to produce a reference voltage derived from the compliance voltage.

3. The system of claim 2, further comprising a capacitance coupled between the reference voltage and the one or more first of the electrodes.

4. The system of claim 3, wherein the biasing circuitry comprises an amplifier.

5. The system of claim 4, wherein the amplifier comprises a first input and a second input and an output, wherein the amplifier is configured as a follower in which the reference voltage is provided to the first input, and wherein the output is provided to the second input.

6. The system of claim 4, wherein the amplifier is configured to maintain the output equal to the reference voltage if a current through the capacitance is between a minimum and maximum output current of the amplifier.

7. The system of claim 3, further comprising logic circuitry configured to issue at least one indication that the reference voltage exceeds a first threshold or falls below a second threshold.

8. The system of claim 7, further comprising control circuitry configured in response to the at least one indication to issue an enable signal indicating when a neural response in the patient's tissue in response to the stimulation current can be sensed at at least one of the plurality of electrode nodes.

9. The system of claim 1, wherein the common mode voltage is approximately half of the compliance voltage.

10. The system of claim 1, wherein the stimulation circuitry is configured to provide the stimulation current through the patient's tissue via the one or more first of the electrodes.

11. The system of claim 1, further comprising a case, wherein the case comprises one of the electrodes.

12. The system of claim 11, wherein the one or more first of the electrodes comprises the case.

13. The system of claim 1, wherein the capacitance comprises one or more capacitors.

14. The system of claim 1, further comprising at least one sense amplifier configured to sense a neural response in the patient's tissue in response to the stimulation current when the common mode voltage is provided at the one or more first of the electrodes.

15. The system of claim 14, wherein the at least one sense amplifier comprises a first input and a second input, wherein the at least one sense amplifier is configured to receive one of the electrode nodes at its first input.

16. The system of claim 15, wherein the at least one sense amplifier is configured to receive the common mode voltage at its second input, or is configured to receive another one of the electrode nodes at its second input to differentially sense the neural response between the one electrode node and the another electrode node.

17. A method of providing stimulation in a stimulator device system, the system comprising a plurality of electrodes, and a plurality of electrode nodes each configured to be coupled to one of the plurality of electrodes, the method comprising:

using stimulation circuitry to provide a stimulation current through the patient's tissue via at least one of the plurality of electrode nodes, wherein the stimulation circuitry is configured to be powered between a compliance voltage and a ground, wherein the compliance voltage varies as a function of time;

sensing a neural response to the stimulation at at least one of the plurality of electrode nodes;

while sensing the neural response, providing a common mode voltage to the patient's tissue at one or more first of the plurality of electrodes, wherein the common mode voltage is derived from the compliance voltage and varies as a function of time.

18. The method of claim 17, wherein the system comprises a case, and wherein one of the one or more first electrodes comprises the case.

19. The method of claim 17, further comprising using biasing circuitry to produce a reference voltage derived from the compliance voltage.

20. The method of claim 19, wherein a capacitance is coupled between the reference voltage and the one or more first of the electrodes.

* * * * *